(12) United States Patent
Van Kalken et al.

(10) Patent No.: US 7,650,290 B2
(45) Date of Patent: Jan. 19, 2010

(54) COMPUTER INSTALLATION FOR ESTABLISHING A DIAGNOSIS

(76) Inventors: Coenrad Karel Van Kalken, De Hout 42, NL-1607 HD, Hem (NL); Roderik Adriaan Kraaijenhagen, Keizer Karelplein 10, NL-1185 HL, Amstelveen (NL)

( * ) Notice: Subject to any disclaimer, the term of this patent is extended or adjusted under 35 U.S.C. 154(b) by 820 days.

(21) Appl. No.: 11/080,339

(22) Filed: Mar. 15, 2005

(65) Prior Publication Data

US 2006/0059015 A1    Mar. 16, 2006

(30) Foreign Application Priority Data

Sep. 15, 2004    (NL) .................................... 1027047

(51) Int. Cl.
*G06Q 10/00* (2006.01)
(52) U.S. Cl. ......................................................... 705/2
(58) Field of Classification Search ................. 705/2–3
See application file for complete search history.

(56) References Cited

U.S. PATENT DOCUMENTS 6,653,140 B2    11/2003    Otvos

| 2002/0022772 | A1 | 2/2002 | Dodds |
| 2002/0029157 | A1* | 3/2002 | Marchosky ..................... 705/3 |
| 2003/0046114 | A1* | 3/2003 | Davies et al. .................. 705/3 |
| 2003/0120134 | A1 | 6/2003 | Rao et al. |
| 2006/0173712 | A1 | 8/2006 | Joubert |

FOREIGN PATENT DOCUMENTS

| GB | 2 352 815 A | 2/2001 |
| WO | WO 97/50046 | 12/1997 |

* cited by examiner

*Primary Examiner*—Gerald J. O'Connor
*Assistant Examiner*—Rajiv J Raj
(74) *Attorney, Agent, or Firm*—The Webb Law Firm

(57) ABSTRACT

A method and computer installation for communicating with one or more other computer installations with a processor, and memory with data and instructions stored therein so that the processor can execute a predetermined program. The program enables the processor to receive the following data: anamnesis data for a client; physical/diagnostic data for the client; data on diagnostic methods; and use of medication and treatment methods with regard to predetermined diseases. The program enables the processor to calculate, and incorporate in a report, the following: the risk of the client acquiring one of the predetermined diseases, harbouring such a disease or having such a disease; data with regard to a possible prevention programme for the client to prevent the one of the predetermined diseases; and data with regard to any medication to combat the one of the predetermined diseases that may be harboured or existing.

25 Claims, 9 Drawing Sheets

■ seriously unhealthy  ▨ moderately unhealthy  ▣ slightly unhealthy  ☐ healthy

■ seriously unhealthy  ▨ moderately unhealthy  ▨ slightly unhealthy  ▢ healthy

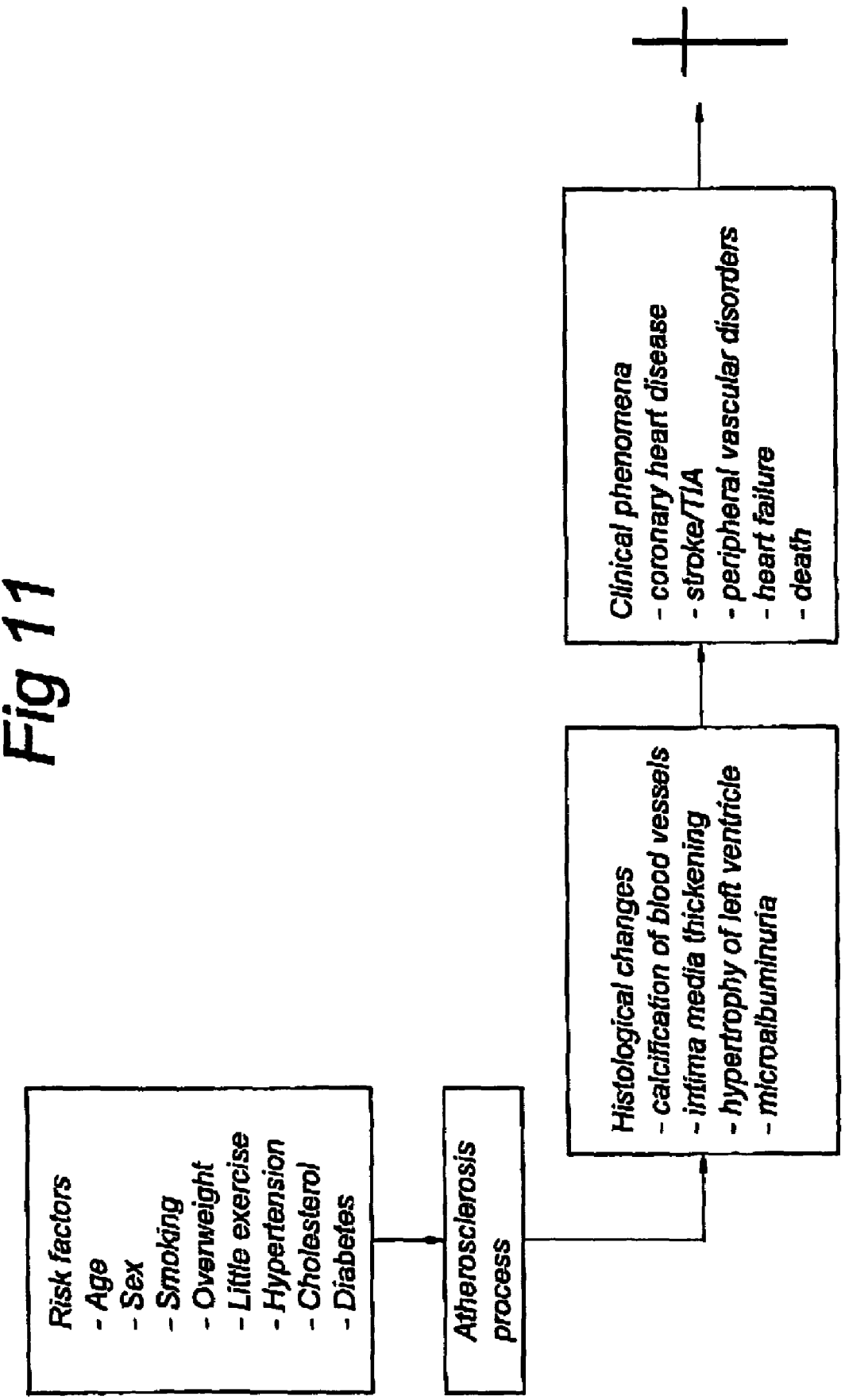

COMPUTER INSTALLATION FOR ESTABLISHING A DIAGNOSIS

BACKGROUND OF THE INVENTION

Increasingly there is scientific insight that early, presymptomatic intervention can emphatically change the biological behaviour of the most important life-threatening disease processes, such as atherosclerosis and many types of cancer.[1-6] Our current healthcare system is as yet mainly fixated on the occurrence of symptoms. However, from the standpoint of the medical process symptoms are no more than a first sign of underlying disease processes that have existed for years and sometimes even throughout the patient's life. In fact, symptoms arise only very late in the natural course of the above-mentioned and other disease processes. There is often then already irreversible organ damage (vascular diseases) or metastasisation that can no longer be cured.

This is further illustrated in FIG. 1, which shows the development of cancer as a disease process. FIG. 1 shows that in a first stage abnormal cells arise, whilst in subsequent stages there will be hyperplasia, dysplasia, a local tumour and a metastasised tumour, respectively. Prevention is still possible at the stages of abnormal cells and hyperplasia, early diagnostics can be carried out at the dysplasia stage, early intervention can take place at the stage of a local tumour and a late intervention can possibly still take place at the metastasised tumour stage.

In practice, therefore, waiting for symptoms often means too late a starting point for effective treatment. The high morbidity that is the consequence of this is associated with high costs and complex treatment. Despite the fact that there is progress in the development of new and more effective treatments and advances are still being made, the costs per year of life gained are high if these treatments are employed only at the end of the disease process. In this context there will, by definition, increasingly be a "reduced marginal return", which ultimately makes a broad-based social discussion on the rationalisation of care offered in the final stage of disease processes unavoidable.

If care is to have a healthy future there will have to be a gradual, but emphatic, shift from "care of the sick" to "healthcare" in the most literal sense. This shift in medical focus is made possible by the rapidly increasing insight into the biology of diseases/disease processes and impressive developments in the field of (early) diagnostics related to this. This progress will increasingly underline the importance of prevention and early intervention.

In many cases symptoms arise only when the tumour impedes the organ function or grows in blood vessels. By definition, the risk of metastasisation, which it may or may not be possible to diagnose, is then high. The representation in FIG. 1 shows disease as a process and illustrates the possibilities for an earlier influence on this. The "atherosclerosis" disease process can be illustrated in a virtually identical manner.

Healthcare in The Netherlands (and beyond) is under severe pressure. Costs continue to rise exponentially, whilst the peak in the aging population has not yet been reached. In 2003 The Netherlands spent almost 10% of the gross national product on healthcare (44 billion Euros).[7-11] A significant proportion of this growing expenditure is accounted for by the treatment of life-threatening complaints such as cancer and heart and vascular diseases, which together account for 60-70% of deaths in the Dutch/Western population.

Healthy life expectancy is approximately the same for men as for women: 61.3 and 60.8 years, respectively. In view of the life expectancy of 75.5 years for men and of 80.6 years for women, this means that women on average live in relative ill health for almost 20 years and men for approximately 14 years. On average, for both men and women, the first symptoms of underlying disease processes start from the age of 50.

FIGS. 2a and 2b show survival curves for men and women, respectively, in 2000. The surface area between the lines represents, from bottom to top, the number of years in good health and in slight, moderate and serious ill health (sources: CBS (Central Bureau voor de Statistiek (Central Office for Statistics) Statistics on causes of death). Life-threatening disease processes can be established at an early (presymptomatic) stage using advanced diagnostic techniques. There are also increasing scientific indications that prevention and/or early (presymptomatic) intervention can emphatically change the biological behaviour of these processes. Therefore, if employed in the correct manner and in the correct disease processes, adequate and early intervention in good time could itself lead, with simple means, to an appreciable gain in health and thus to an increase in (healthy) life expectancy. In theory the "socially active years" can increase significantly and the costs per year of life gained are relatively low, both at the individual and at population level.[7]

An appreciable proportion of the morbidity and mortality in the western world is associated with our lifestyle. At the individual level on average 70-80% of the total medical costs are incurred in the last 5 years of someone's life with a peak in the last year of life. Whilst the total costs of healthcare in 2004 were approximately 44 billion per year, less than 2 billion (<4%) were spent on prevention. This sum includes, inter alia, the vaccination programmes for the prevention of infectious diseases, so that only a small proportion of this sum is available for the prevention of/early diagnostics for heart and vascular diseases and cancer.[7, 8, 11] There is still a great deal to be gained by adequate and cost-effective implementation of early intervention and more preventive measures, both for the individual patient and for the population and for the costs of healthcare in general.[7]

In this context it is extremely valuable that the developments in the diagnostic field in particular have been very rapid in recent years. Unravelling the genetic and molecular backgrounds of diseases has yielded techniques which, on the one hand, can reveal an increased risk of the development of a specific disorder and, on the other hand, can establish early manifestations even before there are symptoms or complaints. Even in the field of instrumental imaging techniques, increasingly more sophisticated techniques are becoming available which have improved sensitivity and resolution compared with the conventional techniques. The possibilities for detecting early, presymptomatic signals of a wide variety of diseases, in the form of genetic, molecular and/or incipient anatomical abnormalities, are emphatically improved as a result.[1, 2, 6, 12] The end of these developments is still a long way off, on the contrary.

Despite the above, there is justifiable hesitation in seeking wider implementation of the conventional preventive "screening model". The current inefficient and expensive logistics for separate screening programmes, combined with scientifically founded drawbacks of conventional screening (overdiagnosis and treatment, high costs, inexpensive but out-of-date and less sensitive techniques, organisational dilemmas, etc.) are all reasons for reticence.

Therefore there is a need for a system with which clients can be screened for diseases that are latent or actually present that does not have the above mentioned disadvantages.

SUMMARY OF THE INVENTION

Therefore, the present invention provides a computer installation provided with an input/output unit for communicating with one or more other computer installations, a processor, and memory with data and instructions stored therein so that the processor can execute a predetermined program, wherein the program is equipped to enable the processor to receive at least the following data:
  anamnesis data for a client;
  physical/diagnostic data for the client;
  data on diagnostic methods;
  use of medication and treatment methods;
to enable the processor to calculate the following on the basis of these data for the client and to enable it to incorporate the results in a report:
  the risk of acquiring one of the predetermined diseases in the future, harbouring such a disease or having such a disease;
  data with regard to a possible prevention programme for the client to prevent the one of the predetermined diseases;
  data with regard to any medication to combat the one of the predetermined diseases that may be harboured or existing;
and to enable the processor to produce the report as output.

An integrated and individualised early diagnostic programme that is based on a personal risk profile algorithm and makes use of sophisticated and state of the art diagnostic techniques can be supported by such a computer installation. Such a computer installation removes the majority of the abovementioned drawbacks.

The computer installation is in line with recommendations to government to pay more attention to (maintenance of) preventive measures and thus to keep the costs of care manageable. The computer installation can advantageously be used by the healthcare consumer who is increasingly aware of the importance of good health, wants to do a lot, but still clearly needs guidance in the direction of health-promoting (preventive) behaviour. The computer installation is also attractive to those providing health insurance. The latter are increasingly responsible for supplying a complete package of care of high quality in which attention is also paid to health management.

BRIEF DESCRIPTION OF THE DRAWINGS

The invention will be explained in more detail below with reference to a few figures, which are intended solely for illustration and not to limit the inventive concept.

FIG. 11 shows the relationship between risk factors and clinical phenomena in heart and vascular diseases.

DETAILED DESCRIPTION OF THE INVENTION

The invention is explicitly based on underlying disease processes and not on the symptomatic diseases in the narrower sense as are defined in conventional organ medicine to date. The concept is based on the increasing scientific foundation that the detection of disease processes in an early stage leads to simpler and, at the same time, more effective treatment. However, in order to make this new approach successful it is also a condition sine qua non that the concept contributes to making the costs of healthcare manageable.

Figure 3:
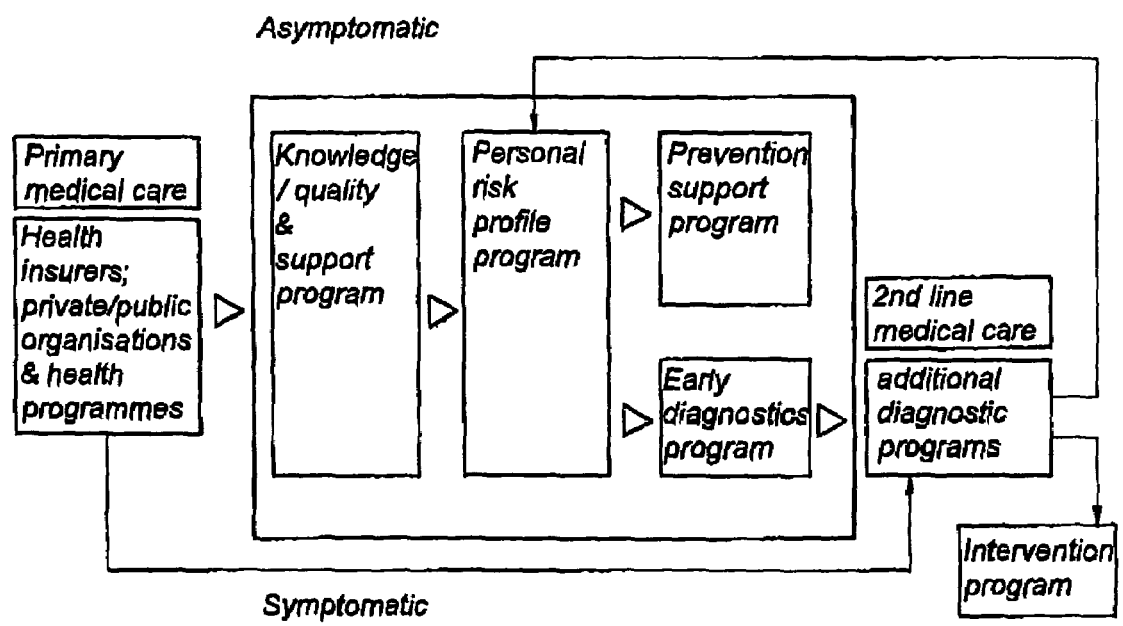
FIG. 3 shows a diagram that illustrates how the installation can be used by medical and non-medical parties.

FIG. 3 shows, diagrammatically, the basic concept in relation to the existing medical and non-medical parties. As will also become clear below, the basic concept is close to primary care practitioners and strengthens their position. General practitioners/company doctors acquire a tool by means of which individuals at high risk can be referred to 2nd line care practitioners in good time or can be guided in a motivated manner specifically more in a direction of health-promoting/preventive measures. 2nd line care practitioners, in turn, are sent a defined asymptomatic population. Symptomatic patients, of course, go directly through to the 2nd line care practitioners. This will now be explained in more detail.

In order to implement the basic concept a system has been developed that objectifies said inter-individual differences in risk of developing frequently occurring and/or life-threatening complaints in an asymptomatic population. The system developed for this purpose (which hereinafter will also be referred to by the term "PreventieKompas" ("Prevention-Compass")) is a statistical/epidemiological knowledge system built up from modern medical/scientific insights in the field of risk factors and disease indicators. The relative importance of these factors/indicators is established and can be updated on an ongoing basis on the basis of scientific developments. The PreventionCompass can thus yield a reliable and personal risk profile for life-threatening disease processes and diseases for each individual. The PreventionCompass is explained here with reference to the most important heart and vascular diseases and oncological complaints, but this is not intended as a restriction on the possible implementation of the invention. It can easily be implemented in or around primary healthcare and/or company healthcare.

In contrast to what generally takes place in the context of a "check-up", the PreventionCompass provides, in terms of degree and number, concrete information providing insight on which effective medical and non-medical policy can be pursued. Regular repetition and monitoring thereof provides a client/patient and care provider with insight into the development of the risk profile over time. The data therefrom can be kept up to date per individual and care professional. In this way it is possible with little effort and at low cost to work on an individualised programme of prevention and/or supplementary early diagnostics and the individual is helped to take responsibility for his/her own health.

The PreventionCompass links the risk profile to personal early diagnosis advice for individuals at high risk and, in addition, can point the way towards preventive or health-promoting measures for larger groups of people.

Figure 4:
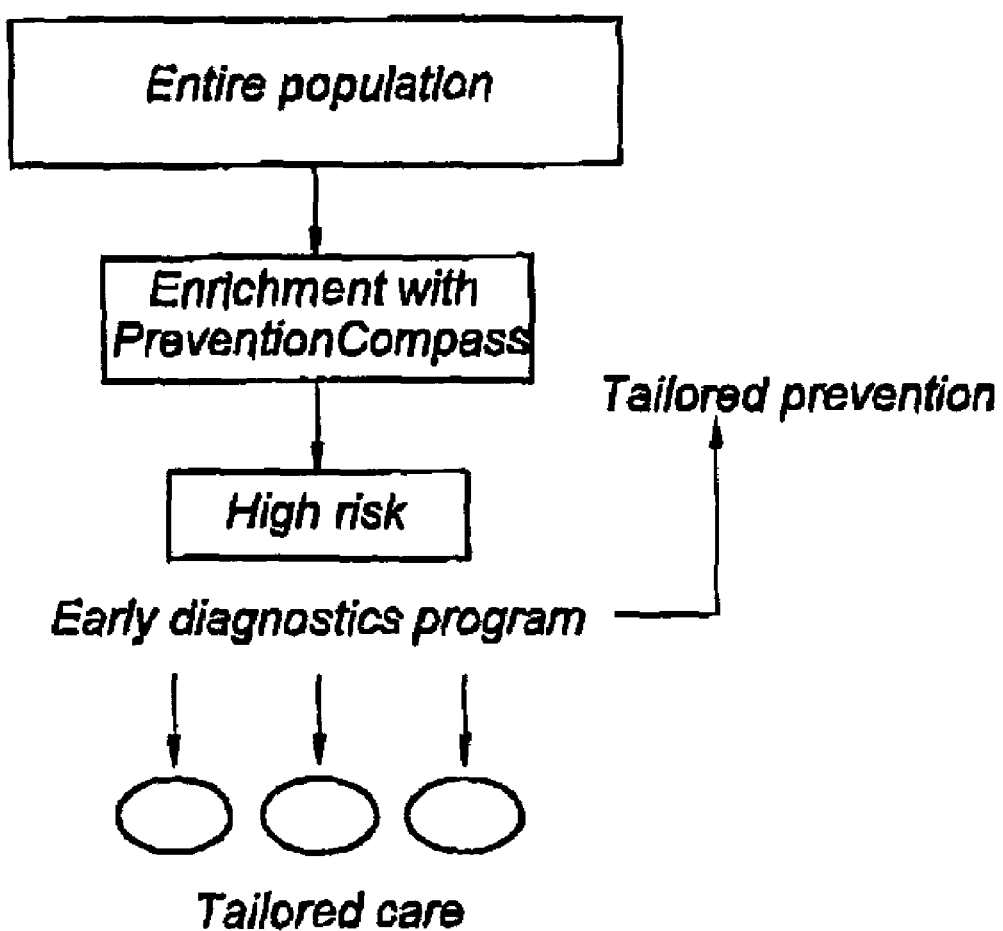
FIG. 4 shows a model for prevention and early diagnostics.

This is illustrated in more detail in FIG. 4. FIG. 4 is a diagram of a prevention and early diagnostics model. As a result of the combination of adequate, personal risk profiling and integrated early diagnostics, high risk patients are "filtered" out of the population in an efficient manner so that referral in good time to 2nd line healthcare becomes possible and "tailored individualised care" can be provided. In addition it provides a guideline and stimulus for "tailored prevention" through insight into underlying (asymptomatic) disease processes and the influence of individual risk factors on these.

Figure 5A:
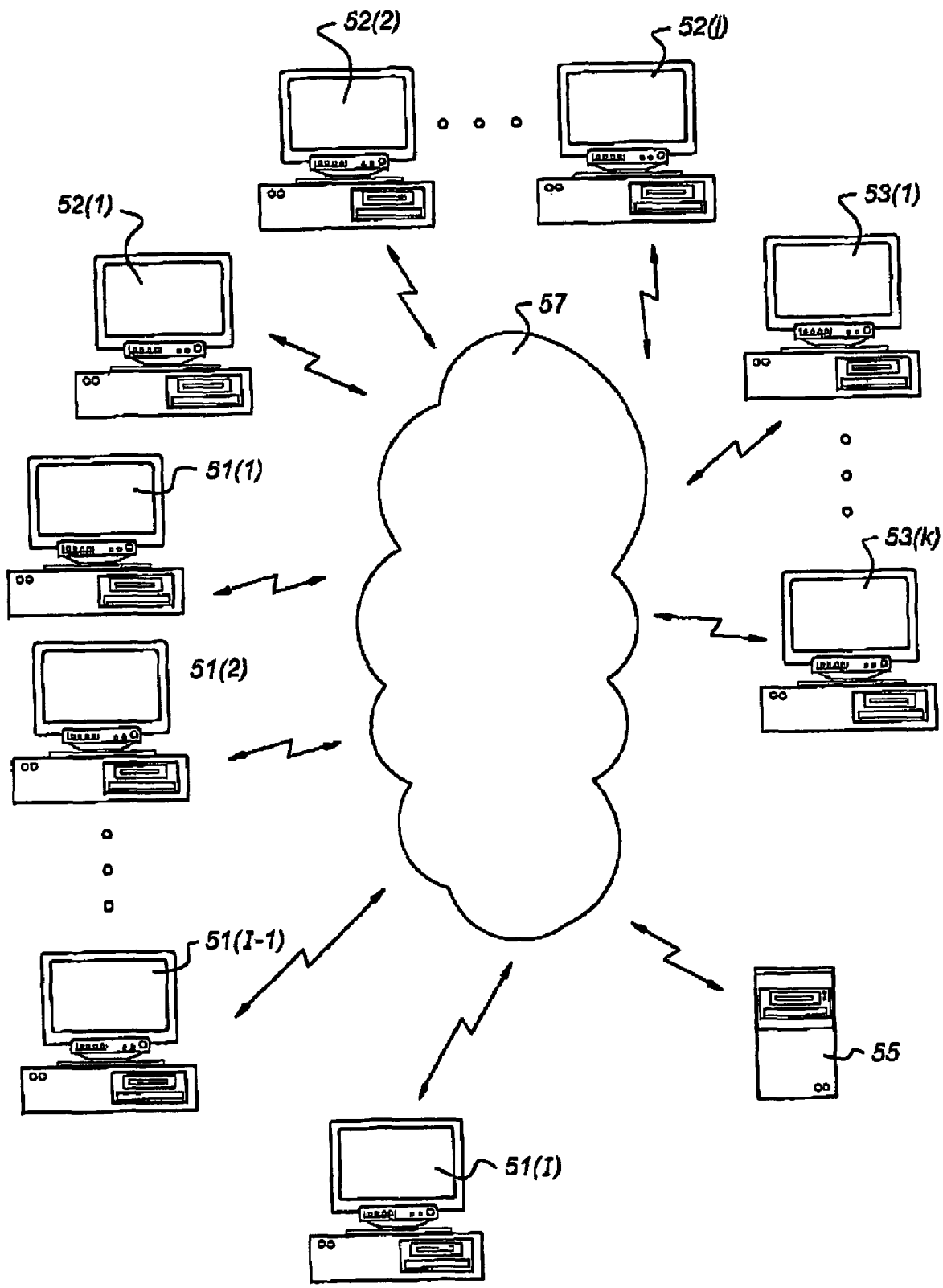
FIG. 5a shows a network system in which the invention can be employed.

FIG. 5a shows a network arrangement by means of which the invention can be implemented. For this purpose FIG. 5a shows a first group of PCs (PC=personal computer) $51(i)$, i=1, 2, . . . , I, a second group of PCs $52(j)$, j=1, 2, . . . , J, a third group of PCs $53(k)$, k=1, 2, . . . , K, and a server 55 that can communicate with one another via a communications network 57. The first group of PCs $51(i)$ are installed at clients, whilst PCs from the second group of PCs $53(j)$ are installed in one or more laboratories and the third group of PCs $53(k)$ are installed in one or more scientific institutes. The server 53 is installed centrally, which, for example, can be in the same room as that where the third group of PCs $53(k)$ are installed.

It is pointed out that the clients' PCs $51(i)$ do not necessarily have to be in the clients' homes. They can actually, for example, also be installed in a general practitioner's surgery. The point at issue is that clients' data can be entered into the system and can be sent to the server 55. The client can do this him or herself on his/her PC at home, but as an alternative a doctor (or somebody else) can do this on behalf of the client on a PC installed elsewhere.

Communication between the various pieces of equipment in FIG. 5a can be via cables but can also be wireless. The network 57 can be any currently known communications network, for example PSTN (Public Switched Telephone Network), a local area network (LAN), a wide area network (WAN), Internet, etc., or any network to be developed in the future. The PCs can be replaced by any telecommunications equipment (for example a computer, a mobile telephone, a PDA=personal digital assistant, etc.) by means of which contact can be made with the server 55 and that is able to offer the functionality described below.

Figure 5B:
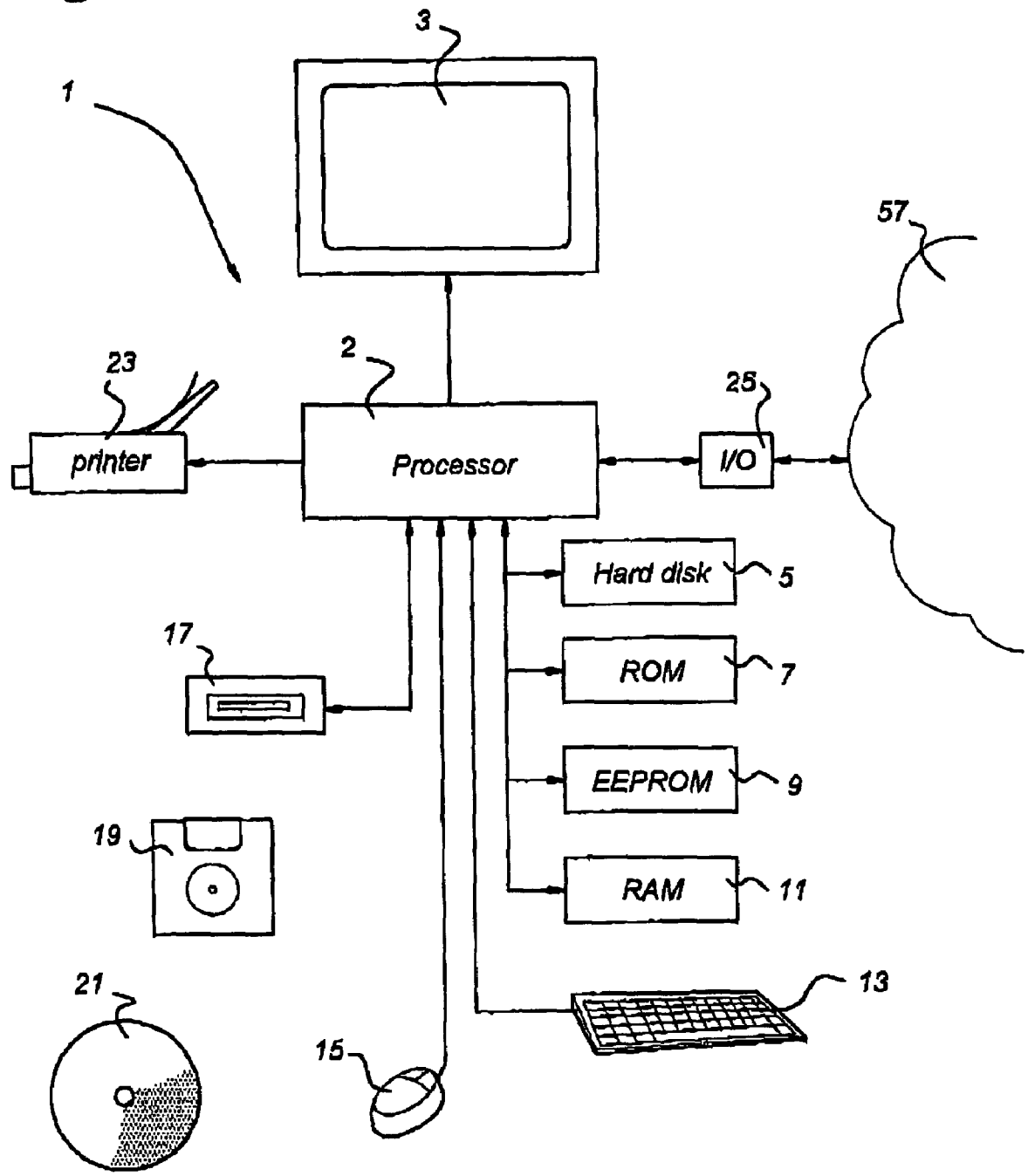
FIG. 5b shows a computer configuration.

The PCs $51(i)$, $52(j)$ and $53(k)$ and the server 55 can have a configuration as set out in FIG. 5b.

FIG. 5b shows a computer installation 1 with a processor 2 for performing arithmetic operations.

The processor 2 is connected to a number of memory components including a hard disk 5, Read Only Memory (ROM) 7, Electrically Erasable Programmable Read Only Memory (EEPROM) 9 and Random Access Memory (RAM) 11. Not all of these memory types necessarily have to be present. Furthermore, they do not have to be physically located close to the processor 2. They can also be located remotely therefrom.

The processor 2 is also connected to means for inputting instructions, data, etc. by a user, such as a keyboard 13 and a mouse 15. Other input means, such as a touch screen, a track ball and/or speech converter, which are known to those skilled in the art, can also be used.

A read/write unit 17 connected to the processor 2 is provided. The read/write unit 17 is equipped to read data from, and optionally to store data on, a data carrier, such as a floppy disk 19 or a CD-ROM/CD-R 21. Other data carriers can be, for example, DVDs (DVD-R, DVD+R), as is known to those skilled in the art.

The processor 2 is also connected to a printer 23 for printing output data on paper, and to a display unit 3, for example a monitor or LCD (Liquid Crystal Display) screen or any other type of display unit known to those skilled in the art.

The processor 2 is connected to the communications network 57 by means of input/output means 25. The processor 2 is equipped to communicate with other communication devices via the network 57.

The processor can be implemented as a stand-alone system or as a number of processors operating in parallel and each of which is equipped to perform sub-tasks from a larger program, or as one or more main processors with diverse subprocessors. Parts of the functionality of the invention can even, if desired, be implemented by processors located remotely that communicate with processor 2 via network 57.

Each of the various groups of PCs $51(i)$, $52(j)$, $53(k)$ can be used to input different types of data and to send these to the server 55. The server 55 has data and instructions stored in its memory by means of which a web site can be made available to the PCs $51(i)$, $52(j)$, $53(k)$. The users of the PCs $51(i)$, $52(j)$, $53(k)$ answer questions that are posed on this web site. The parts to which each of the users can gain access are preferably protected from one another, for example by use of login names and passwords, or in any other known manner. Certainly personal details will be stored on the server 55 with good security.

The type of data that have to be sent to the server 55 can roughly be split into two different types: client details and scientific data. The client details are certainly private and are input using the PCs $51(i)$, $52(j)$. The following types of data are input via the client PCs $51(i)$ (see also FIG. 6):

a. personal details 61, including at least:
name and address data;
data relating to psychological and characterological characteristics and characteristics determining behaviour.

b. anamnesis data 62, including at least:
data with regard to previous medical history and medication;
lifestyle data;
medical data with regard to family.

The following data can be input via the PCs $52(j)$, which have been installed in laboratories, and sent to the server 55 (see also FIG. 6):

a. Data on Physical/Diagnostic Examination 63
These comprise at least simple examinations such as blood pressure measurement, height measurements, weight measurements, waist measurements, heart rate measurements, etc. It will be clear that such an examination can also be carried out by a nurse or general practitioner and that the PC $52(j)$ used for this is installed at an agency where such objective measurements can be carried out.

b. Data From Laboratory Tests 64
These are tests that take a longer time or require specific equipment, such as clinical chemical tests, urine tests, faeces tests, etc.

The following data can be input via the PCs $53(k)$, which are installed in scientific institutes, and sent to the server 55 (see also FIG. 6):

a. Data Relating to Diagnostic Methods 65
these are, for example, data relating to reliability and safety of (early) diagnostic methods to be used, such as sensitivity, specificity, negative and positive predictive value, side effects and complications.

b. Data with Regard to use of Medication and Treatment Methods 66
These are, for example, data relating to effectiveness, side effects and complications of treatment methods and medication used, including in the past.

c. Financial/Economic Data 67

These are data relating to cost effectiveness, including healthcare costs, specific disease treatments and possibly socially acceptable costs.

d. Client Preference 68

These can be entered by a client (or someone else) and relate, for example, to preferences with regard to:
  the degree of supplementary (invasive) diagnostics that is acceptable to the client in order to arrive at a definitive diagnosis,
  diagnostic techniques with a comparable result (for example traditional coloscopy and virtual coloscopy with CT scan)
  treatment methods (for example tablets or injections), etc.

Figure 6:
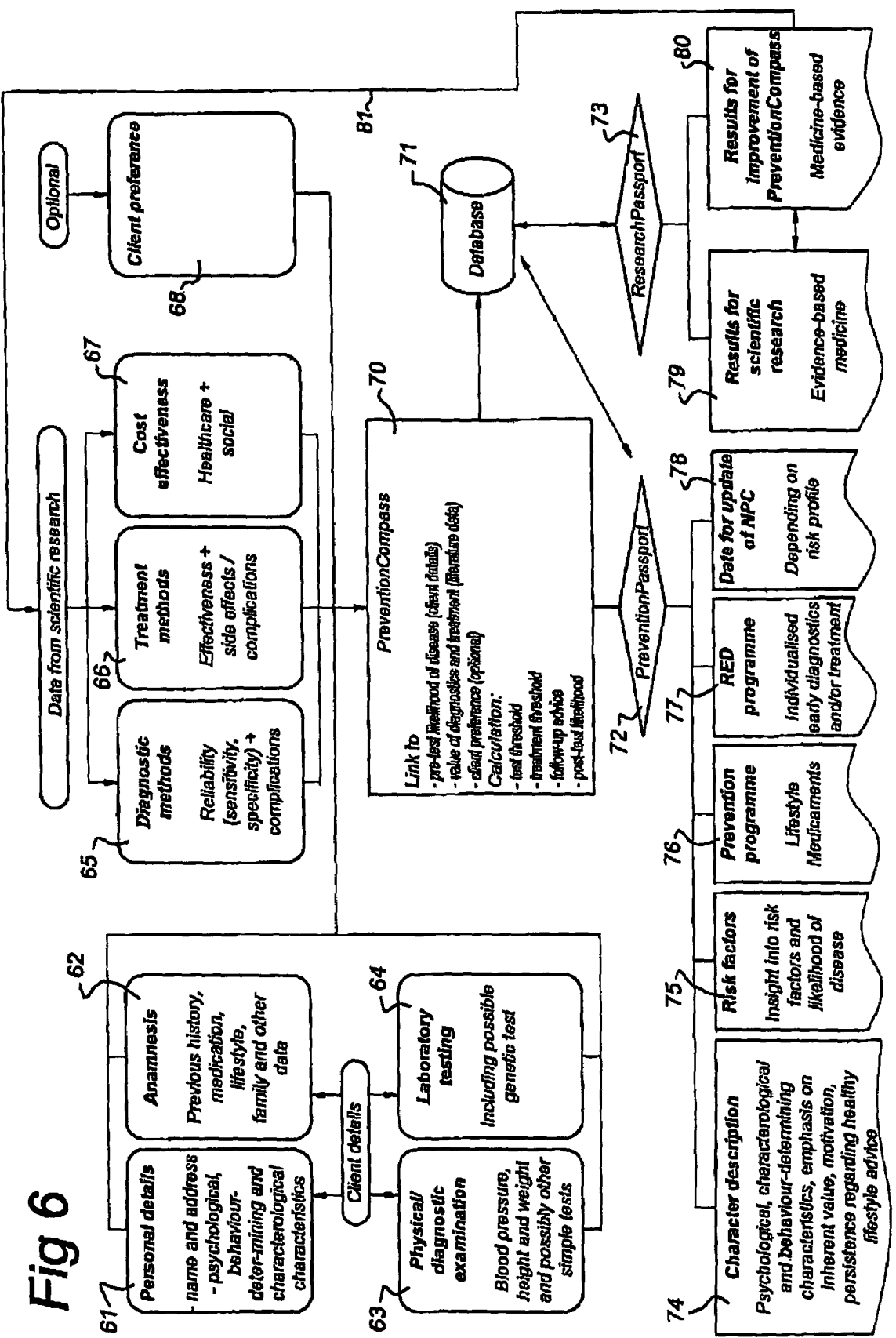
FIG. 6 shows a flowchart of an example of a method according to the invention.

FIG. 6, which shows the data flows and calculations in the system in FIG. 5a, shows that all these data go to a block 70. The block 70 is the model for the abovementioned PreventionCompass and relates to the functionality of server 55. The server 55 produces a personal "PreventionPassport" 72 on the basis of all data received and produces a "ResearchPassport" 73 with the aid of the PreventionCompass. The significance of this will be explained below.

On the basis of the client data 61, 62, 63, 64 received and the data from scientific tests 65, 66, 67, the server 55 determines a pre-test likelihood of a particular disease and (optionally) establishes the client's preference. On the basis of the client details and the data from the scientific institutes, the server 55 then calculates the following via the calculation models to be explained in more detail: a test threshold for supplementary early diagnostics (including the post-test risk of disease depending on the result), a treatment threshold for possible medical treatment(s) and a follow-up recommendation.

The result of the calculations is summarised in the PreventionPassport 72 and the ResearchPassport 73, both of which are stored in a database 71 in the memory of the server 55.

The PreventionPassport 72 contains the following data:
  psychological and characterological characteristics and characteristics determining behaviour with the emphasis on inherent value and motivation and persistence regarding advice on a healthy lifestyle (as aids for influencing behaviour);
  risk factors, that is to say insight into risk factors and risk of a specific disease;
  prevention programme, possibly including advice on lifestyle and advice on medicines;
  "RED program" data 77 ("Risk-based Early Diagnostic program") containing data on any impending disease (individualised early diagnostics);
  recommended date/term for repeating the PreventionCompass.

The ResearchPassport 73 contains the following data:
  results that are (can be) important for scientific research 79 (evidence-based medicine);
  results 80 that can be of importance for improvement of the PreventionCompass 70 (medicine-based evidence).

An arrow 81 indicates that the results 79 and 80 can be fed back, optionally on request, to the PCs 53(k) of the scientific institutes.

All of this will be explained in more detail below.

Since the PreventionCompass links the personal risk profile directly to an individualised prevention and/or early diagnostics programme (in the case of high risk individuals), the preventive/early diagnostic path becomes not only more (cost-)effective but also more reliable. The reason for this is because there is a clear relationship between the "pre-test likelihood" of disease and the chance that a diagnostic method will also actually show the disease. This is explained in more detail below in "the medical/scientific foundation for the concept".

In one embodiment the information obtained by means of the PreventionCompass is accessible with an option for feedback to both carer professionals and scientists and also in an increasing extent to the individual (the client/patient) him or herself. The information must therefore be, in particular, clear, user friendly and up-to-date and based on specific questions from clients and medical professionals. The output from the PreventionCompass 72 and the early diagnostic program thus constitutes the most important input for a transmural personal (electronic) patient file (EPF) with dynamic guidelines. A dynamic guideline is based not only on scientific knowledge but also on practical information and can be designed and updated more rapidly than is usually the case with guidelines.

The dynamic guidelines can be kept up to date centrally and continuously on the basis of "evidence-based medicine" and cost-effectiveness. This yields an effective and up-to-date electronic patient's file supporting decisions and process.

Decentralised input of (individual client) data 61-68 with central storage of the data in database 71 generates a wealth of information. From this continuous stream of information it is possible to derive the outcomes, such as clinical outcomes, but also information on patient satisfaction, efficiency and cost-effectiveness, on the basis of which the care process can be further adjusted (controlled) ("medicine-based evidence"). This client-oriented Electronic Patient's File, in which the generic and fixed "evidence-based medicine" is integrated with the individual and flexible "medicine-based evidence" will thus be able to play a major role in obtaining basic medical evidence.

An important point for consideration in the above context is medically/scientifically justified application of existing and new techniques in the context of early diagnostics. Many more recent techniques are highly promising but the precise value (or lack of this) thereof for risk profiling and/or early diagnostics still has to be yet further investigated. The approach proposed here yields the ideal infrastructure for scientific research in this field. A protocolled stream of patients and thorough follow-up also creates new possibilities for large-scale scientific research into the etiology of the underlying complaints and the extent to which these can be influenced.

The Medical/Scientific Foundation for the Concept

In the following paragraphs it is outlined how the various starting points have been handled in the development of the invention. It is also indicated how the provisional list of complaints and associated early diagnostic techniques was arrived at.

Screening on the Basis of a Personal Risk Profile: NIPED Early Diagnostics

The invention relates to a novel form of early diagnostics for asymptomatic complaints. For this purpose a model has been developed that differs both from (conventional) screening and also from so-called opportunistic screening (case finding).

Conventional Form of Screening

Screening (literally: critical examination) was defined in 1951 by the US Commission on Chronic Illness as:
  "The early identification of an as yet unrecognised disease by means of tests, examinations or other procedures that can be carried out rapidly. The aim of screening is to distinguish between apparently healthy individuals, who may nevertheless have a specific disease, and those who do not have this disease. It is not the intention of a screening test to make a diagnosis. Any person with a positive test must be referred to his/her doctor for further examination, diagnosis and treatment."

In 1993 this definition was refined by the WHO (World Health Organisation) and, without substantially changing the determination of 1951, in this definition it is pointed out that screening is always initiated by care professionals and not by the patient. Thus, a great deal of caution must be exercised in generalisation of specific measures.

Current Forms of Screening

In the new definition a distinction is made between "screening" and "opportunistic screening" (case finding), each with its own drawbacks and advantages:

The definition of screening is: the early identification of an as yet unrecognised disease in an unselected population. The aim is to make a distinction between apparently healthy individuals, who possibly nevertheless have a specific disease, and those who do not have this disease. The "screening performer" (the person who examines the client) has no responsibility for the follow-up of abnormal test results; each person with a positive test is referred to his/her doctor for further examination, diagnosis and treatment.

This screening is subject to the following drawbacks:
Unselected population, as a result of which a priori the chance of disease is very low, with the consequence of many false positive test results, overdiagnosis and medical treatment.
No responsibility and follow-up.

The following advantages of this screening may be mentioned:
Intended broad coverage of population.
Intended guarantee of quality as a result of uniform objective approach and clear guidelines.

The definition of opportunistic screening (case finding) is as follows: the early identification of an as yet unrecognised disease under the responsibility of a physician and carried out in the physician's own patient population. What is concerned here is a selected group of patients, although without clear selection criteria. Use is made of tests, examinations or other procedures that can be carried out rapidly. This is intended for risk factor identification without it being the intention to make a diagnosis. Since the relationship concerned is a doctor/patient relationship there is a clear responsibility for the follow-up of abnormal test results.

The advantages of opportunistic screening compared with screening are:
More or less selected population, as a result of which there is a higher a priori chance of disease and thus fewer false positive test results, overdiagnosis and medical treatment. Responsibility and follow-up guaranteed.

The following drawbacks of case finding may be mentioned:
Selection criteria are not clear and are not unambiguous, as a result of which an objective estimation of the a priori risk is not possible, with, as a consequence, still an unnecessarily high number of false positive test results, overdiagnosis and medical treatment. Greater risk of missing individuals at risk.
Guarantee of quality is not possible because of subjective approach in the absence of (or limited adherence to) guidelines.
No intended population coverage. Patients who (for one reason or another) do not see a doctor will be missed.

In order to benefit from the advantages of both forms of screening and to restrict the drawbacks as far as possible, a new approach is proposed here: "Early diagnostics on the basis of risk profiling". The definition of this is: the early identification of an as yet unrecognised disease under the responsibility of a physician by means of diagnostic techniques and methods. It is a two-step approach that is concerned here. In a first step high risk individuals are filtered out of the general population, at their own instigation or on the advice of a (general) practitioner treating them, with the aid of the protocolled and validated risk algorithm as supported by the PreventionCompass 70. In a second step targeted supplementary diagnostics are then performed on the enriched risk population using sophisticated equipment in an integrated setting, that is to say in a laboratory from which the physical/diagnostic examination data 63 and/or the laboratory investigation data 64 result. It is important that the responsibility for the follow-up of abnormal test results is borne by a physician and that this follow-up is guaranteed by integration/close collaboration with primary and 2nd line healthcare.

This is thus a "Best of both worlds" approach:
Objectified estimation of the a priori risk, as a result of which a reliable estimate can be made of the benefit of supplementary diagnostics for the individual, with, as the consequence, minimisation of false positive test results, overdiagnosis and medical treatment.
Quality guaranteed by uniform and objective approach with clear guidelines.
Responsibility and follow-up guaranteed.
Applicable to the entire population.

The following potential risks and adverse effects of early diagnostics may be mentioned:

1] The diagnosis is incorrect (false positive or false negative test result) and patient is unjustifiably treated or not treated.

In this context it is most detrimental for the patient if a diagnosis is made unjustifiably (false positive test result). Firstly because of the "stigma" (see 3) that the patient acquires through this. Secondly because of the fact that a treatment follows unjustifiably, which in itself can already be stressful, but also is associated with the risk of treatment complications. Awareness that the rarer the disease the greater will be the risk of a false positive test result is important in this context.

It is less serious, but nevertheless also very annoying, if the underlying disease is missed (false negative test result) and unjustifiably no treatment is started. The fact that the patient would also not be treated without the early diagnostics lessens the harm to some extent.

2] The treatment that is started has a harmful (side) effect.

Every treatment has potential side effects and can be very stressful (independently of the side effects). Consider, for example, an operation to remove a tumour followed by possible radiation therapy or chemotherapy. If this treatment is started because of a diagnosis that is correct, these negative aspects will be annoying but acceptable. Of course, this is different if the diagnosis was made incorrectly and the treatment is therefore essentially unjustified.

3] The patient who previously felt healthy is stigmatised as being sick.

This can have a direct negative psychological effect on the patient. He/she can take on "the sick role" and consequently feel ill more often. Minor complaints and pains previously ignored can now become an important source of feeling unwell and taking time off work because of sickness. If the diagnosis is correct and the treatment effective the patient will be prepared to live with the "stigma" because the final result is worth it. If, however, the treatment does not work or is not more effective in the early diagnostic stage than in the clinical (symptom) stage, "healthy time" is taken from the patient unnecessarily and he/she is actually merely ill for longer.

Wilson and Jüngner Criteria for Restricting the Potential Negative Consequences of Early Diagnostics In order to avoid the abovementioned pitfalls, two epidemiologists Wilson and Jüngner drew up, at the request of the WHO, ten criteria which early detection investigations must meet to make large scale investigations on the population worthwhile.

| Criteria with regard to disease | 1] relevant<br>2] high prevalence of the pre-clinical stage<br>3] natural course known<br>4] long period between the first signs and the manifest disease |
|---|---|
| Diagnostic test | 5] high sensitivity and specificity<br>6] simple and inexpensive<br>7] safe and acceptable<br>8] reliable |
| Diagnosis and treatment | 9] effective, acceptable and safe treatment available<br>10] adequate facilities |

Re 1] and 2]: The Problem Must be RELEVANT.

The disease to be detected must be one of the major health problems. It is clear that large scale investigations on the population are not the most appropriate means of detecting rare diseases. In that case there is no relationship between the costs and the benefits.

However, there are exceptions to this rule: in particular phenylketonuria is an extremely rare disease and nevertheless infants are generally screened for this. Early detection is useful here because a serious handicap can be prevented here by means of a diet.

Re 3]: Natural Course and Epidemiology Must be Known.

The natural course of the disease to be detected must be known. This is not so evident in current Western society: all serious diseases are in any case treated as soon as they are discovered. The corollary of this is that unfortunately much less is known than we would wish with regard to the natural course of these complaints.

If early screening for cervical cancer detects a picture of carcinoma in situ this is virtually always treated. This does not alter the fact that it is known that this condition is very frequently found to heal spontaneously.

Re 4]: There Must be a RECOGNISABLE LATENT Stage.

There must a recognisable latent stage if detection is to be worthwhile. The latent stage is the time that elapses between the appearance of the very first cancer cell and the first symptoms. A large number of malignant cells can be found in this stage before they have disseminated.

Re 5]: High Sensitivity and Specificity

We must have a usable detection method. An ideal test has a high sensitivity (i.e. few false negatives) and a high specificity (i.e. few false positives) at one and the same time.

For example, there is a very usable test for the detection of cervical cancer. Up to now there is no single acceptable test for large scale early detection of carcinoma of the head of the pancreas.

Re 6]: Cost-Benefit Relationship

The costs must be proportional to the benefits. However, the majority of early detection tests cost more money than they save. What is regarded as reasonable is a social/ethical discussion.

Re 7]: Acceptability

The early diagnostic method will succeed only if it is acceptable to the population. The majority of detection tests that general practitioners have in their arsenal are very acceptable to the population. In America, for example, primary healthcare professionals make substantial use of the sigmoidoscope. However, it is doubtful that the Dutch population would accept this test.

Re 8]: Diagnosis: Who is ill?

There must agreement on who must be regarded as ill. There are instances where a test result is liable to diverse interpretations.

For example, the cholesterol level is extremely important in the evaluation of the risk factors for heart and vascular diseases. The limiting values have been adjusted recently. Anyone with a cholesterol level above 5 mg/l has a raised level, whilst previously the limit was 6 mg/l. Some doctors continue to use the old standards, others have adopted the new.

Re 9]: Treatment

The disease must be treatable with the aid of a generally accepted treatment method if it is to come into consideration for large scale screening. This treatment method must be able to improve the prognosis of the disease.

Re 10]: Facilities

There must be adequate facilities to conduct the diagnosis and treatment that are suitable for the disease to be detected.

4-Step Strategy

The above criteria clearly indicate the framework outside which screening is not effective. However, they are too general to fill in the details of early diagnostics in a responsible and effective manner within this framework. Therefore, in order to make the criteria concrete and applicable to day-to-day practice a strategy that is statistically and epidemiologically sound has been developed. Complaints and the diagnostic method(s) to be used for these will be included in the strategy only if there is compliance with a 4-step strategy specified below for the prevention of negative (mental and/or physical) consequences of early diagnostics.

Step 1: Rough Delineation

Step 1 leads to rough delineation of diseases and methods with the aid of the following criteria:

A. 'Medical urgency': which diseases are responsible for a high percentage mortality and/or are associated with significant harm to the person or society?

B. 'Technology': which early diagnostic methods are there by means of which these diseases can, in principle, be detected early?

C. 'Scientific evidence': how 'hard' or 'soft' is the evidence that the use of these early diagnostic methods is able to prevent death and/or illness and in what populations has any evidence been obtained?

D. 'Feasibility': is it feasible (technologically, financially/economically, organisationally, etc) also actually to implement a technique for which the evidence is considered to be sufficient?

Re A: Medical Urgency

There is a great difference in the personal and social impact of various diseases. Initial 'sifting' on the basis of the severity of diseases and their impact will lead to a justified restriction of the scope of the subsequent steps B to D. The medical urgency can be tested on the basis of the following criteria:

Is the disease/complaint serious?

In this context a complaint is deemed to be serious if it is associated with high morbidity and/or a high mortality amongst the Dutch population. This criterion serves to include those diseases that result in substantial personal and social harm in the form of mortality, morbidity and costs.

Can the disease/complaint for which early diagnostics are carried out be treated or not?

From the medical standpoint there is little point in knowing that someone is suffering from a disease that cannot be treated. The treatability criterion must be applied to the disease in early stages (the stages in which it an attempt is made to detect the disease). This is not necessarily the same as treatability of the same disease in a later stage.

Is the prevalence of the disease/complaint sufficiently high in the population to be tested?

In other words is there a reasonable chance of finding people who have the disease for which screening is carried out via early diagnostics? This partly determines the effectiveness of a diagnostic method. Rare complaints, although sometimes serious, are excluded by this criterion. The consequence of the application of this criterion is that the client can be given no 'absolute guarantee of health'.

Heart and vascular diseases and cancer are the undisputed top two in this classification, followed by disorders of the respiratory tract (Table 1).

TABLE 1

Most important causes of death in The Netherlands in 2000

| Cause of death | No. of persons | % |
|---|---|---|
| Heart and vascular diseases | 49,952 | 36% |
| coronary infarction | 12,959 | |
| stroke | 12,275 | |
| other heart and vascular diseases | 24,718 | |
| Cancer | 37,746 | 27% |
| Diseases of the respiratory organs | 14,677 | 10% |
| Other causes | 38,152 | 27% |

Source: CBS/Nederlandse Harstichting

TABLE 2

Annual incidence, prevalence score (both based on care registrations), mortality and years of life lost; standardised for the Dutch population in 2000 (absolute figures). (Sources: see notes)

| Disease/complaint | | Incidence | Prevalence | Absolute mortality | Years of life lost |
|---|---|---|---|---|---|
| New tissue growth[6] | | | | | |
| Cancer of the oesophagus | M | 740 | 650 | 871 | 12,484 |
| | F | 310 | 360 | 354 | 4,887 |
| Stomach cancer | M | 1,500 | 5,100 | 1,031 | 12,518 |
| | F | 780 | 3,700 | 688 | 8,906 |
| Colon and rectosigmoid cancer | M | 4,800 | 28,000 | 2,140 | 25,695 |
| | F | 4,300 | 28,500 | 2,160 | 26,704 |
| Lung cancer | M | 7,100 | 16,700 | 6,297 | 77,183 |
| | F | 2,190 | 3,200 | 2,262 | 42,423 |
| Skin cancer | | | | | |
| melanoma | M | 940 | 7,200 | 322 | 6,236 |
| | F | 1,310 | 12,900 | 226 | 4,208 |
| squamous cell carcinoma | M | 1,980 | 12,400 | See melanoma | See melanoma |
| | F | 1,250 | 6,700 | See melanoma | See melanoma |
| basal cell carcinoma | M | 6,900 | a | d | d |
| | F | 7,100 | a | d | d |
| Breast cancer | F | 10,500 | 95,000 | 3,425 | 61,233 |
| Prostate cancer | M | 6,800 | 31,700 | 2,367 | 19,044 |
| Non-Hodgkin's lymphoma | M | 1,140 | 5,900 | 600 | 9,174 |
| | V | 970 | 5,400 | 525 | 7,742 |
| Diseases of the cardiovascular system | | | | | |
| Coronary heart disease[10] | M | 40,600 | 337,600 | 9,921 | 115,039 |
| | F | 32,300 | 219,000 | 7,522 | 71,707 |
| Heart failure | M | 18,200 | 50,400 | 2,406 | 17,843 |
| | F | 20,500 | 86,000 | 4,052 | 26,048 |
| Stroke[11] | M | 13,700 | 67,900 | 4,730 | 43,413 |
| | F | 18,200 | 71,800 | 7,545 | 64,344 |
| Aneurism of the abdominal aorta[3,12] | M | 5,700 | b | 620 | 5,490 |
| | F | 1,100 | b | 210 | 1,800 |

The incidence, prevalence, mortality and years of life lost for the most prevalent and treatable forms of cancer and heart and vascular diseases are then shown in Table 2. These figures were obtained from general practitioner registrations and other care registrations. Data that are as recent as possible have been used. In some cases, however, recent figures were not available; in this case the figures from an earlier date were used. The epidemiological characteristic values have been standardised for the population in The Netherlands in 2000. Prevalence and incidence figures higher than 2,500 have been rounded to the nearest 100, figures below 2,500 to the nearest 10.

Re B. Technology

An evaluation is carried out per disease profile or disease field to determine which relevant techniques exist and how these are possibly already used in the diagnostic setting. In this context it is important to list all diagnostic techniques, including the very simple, such as anamnesis and standard blood and urine tests.

Re C. Scientific Evidence

Per diagnostic technique it will have to be investigated whether, in the setting of early diagnostics, this has a proven value on which the evidence is based or, if 'hard' evidence has not been provided, there are provisional indications that the technique concerned could be of value. A difficult part of this exercise is weighing the available evidence, certainly if this has not been obtained in randomised studies. This weighing should result in a medically founded recommendation as to whether or not (yet) to include the technique in the package. In the light of the multiple possibilities for interpretation of scientific evidence serious consideration must be given to first submitting a recommendation formulated in this way to teams of top medical experts, preferably specialising in different fields, before actually including the technique concerned in the database 71.

Re D. Feasibility

The most advanced diagnostic techniques require complex, expensive equipment and sometimes special technical and structural facilities, specially trained laboratory assistants, etc. In the light of the sometimes high costs that can be associated with the implementation of advanced screening techniques, a financial/economic analysis of every new technique is carried out. A relative advantage is that various expensive technologies (for example spiral CT, CT=computer tomography) can be employed in the early diagnostics for various complaints. This means that, following the decision to implement a specific advanced technology, it is sensible to go back to step C, but then for complaints that in the first instance were left out of consideration on the basis of the criteria under A.

The aim of Steps 2 and 3 is to restrict the number of unnecessary tests/examinations as far as possible. Since, as explained above, each test has the chance of a false positive and false negative result it is extremely important to determine in advance, per individual and per disease, whether a specific diagnostic test actually has added value. In this context it is the case that the more adequate the use of a diagnostic test the lower is the risk of the abovementioned pitfalls of early diagnostics.

Step 2: Further Specification of Diseases

The purpose of Step 2 is, following the rough delineation of diseases with the aid of step 1, to arrive at a further specification of diseases for which early diagnostics could be of benefit.

For this purpose the natural course of disease must be taken into consideration so as then to determine on the basis of intrinsic "critical treatment points" whether early diagnostics are worthwhile.

Figure 1:
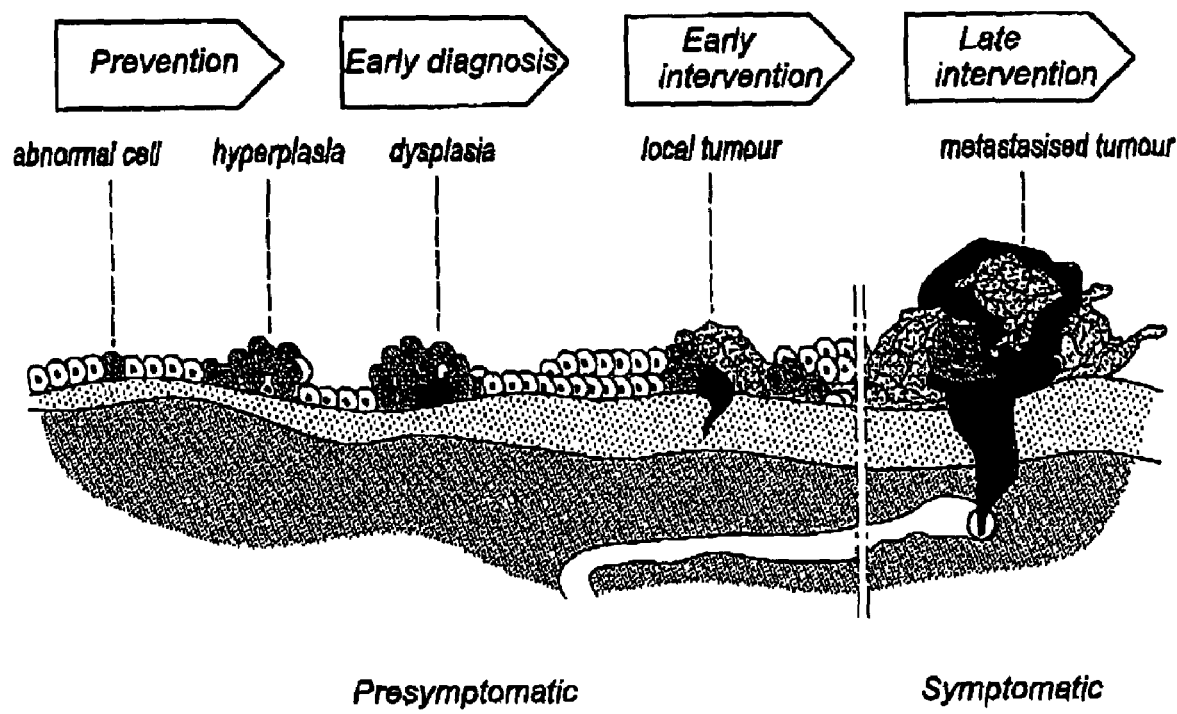
FIG. 1 shows, diagrammatically, the disease process for cancer.

Diagrammatically, the natural course of disease can be subdivided into 4 stages (see FIG. 1):

Stage 1: Biological Onset of the Disease

The disease is already present but cannot yet be discovered with the aid of the current diagnostic tests. In the case of some diseases the time of biological "onset" is during conception; in the case of many other diseases the disease arises only in the course of subsequent life.

Stage 2: Early Diagnostics Possible

The disease is associated with structural or functional changes of a nature such that it is possible, if the correct test is used, to make an early diagnosis.

Stage 3: Onset of Symptoms

If left untreated and there is no spontaneous regression, the disease will progress and symptoms will arise at a given point in time. The person becomes ill, as a result of which it becomes possible to make a clinical diagnosis.

Stage 4: Final Stage of Disease

Finally the disease will reach its final stage in the form of death, recovery with permanent injury or cure.

Figure 2A:
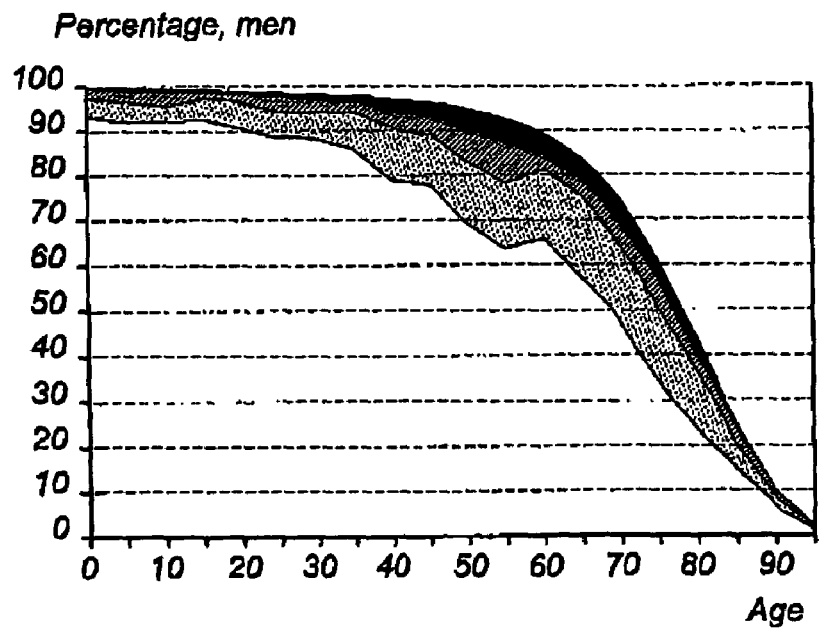
FIGS. 2a, 2b present survival graphs for men and women respectively, again for the year 2000.
Figure 2B:
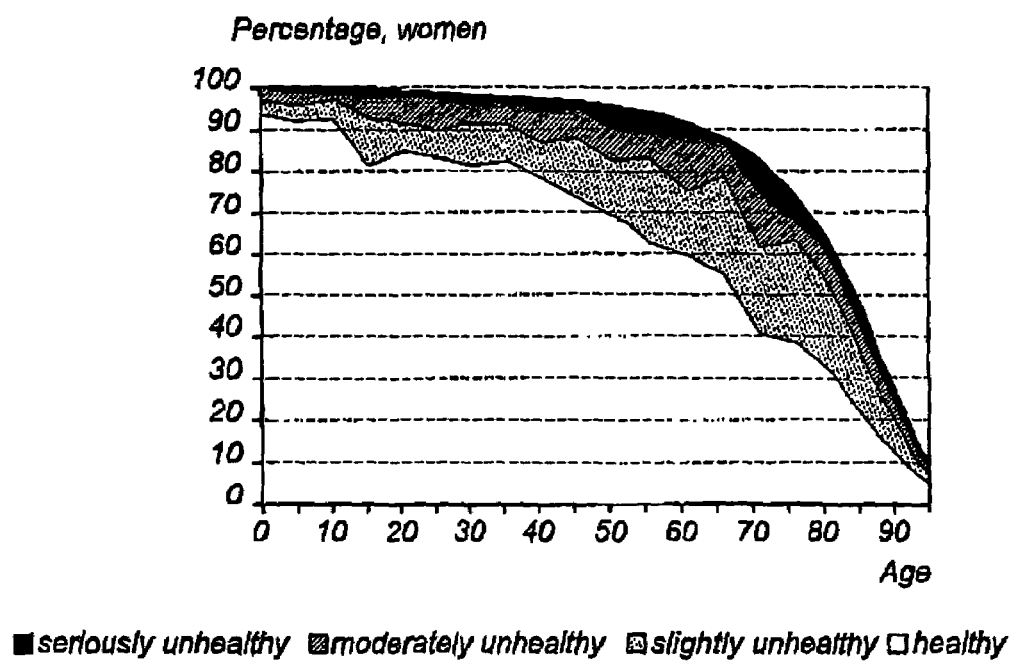
Figure 7:
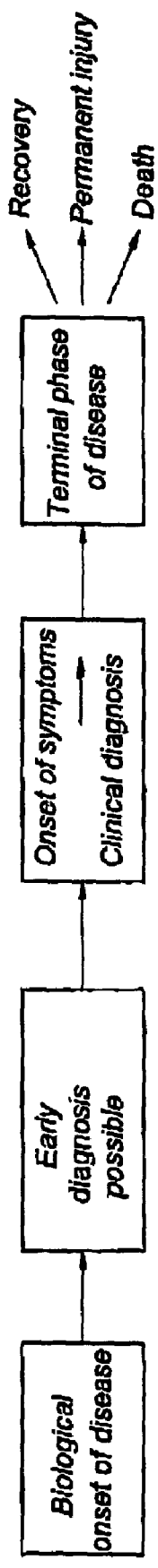
FIG. 7 shows the natural course of a disease.
Figure 8:
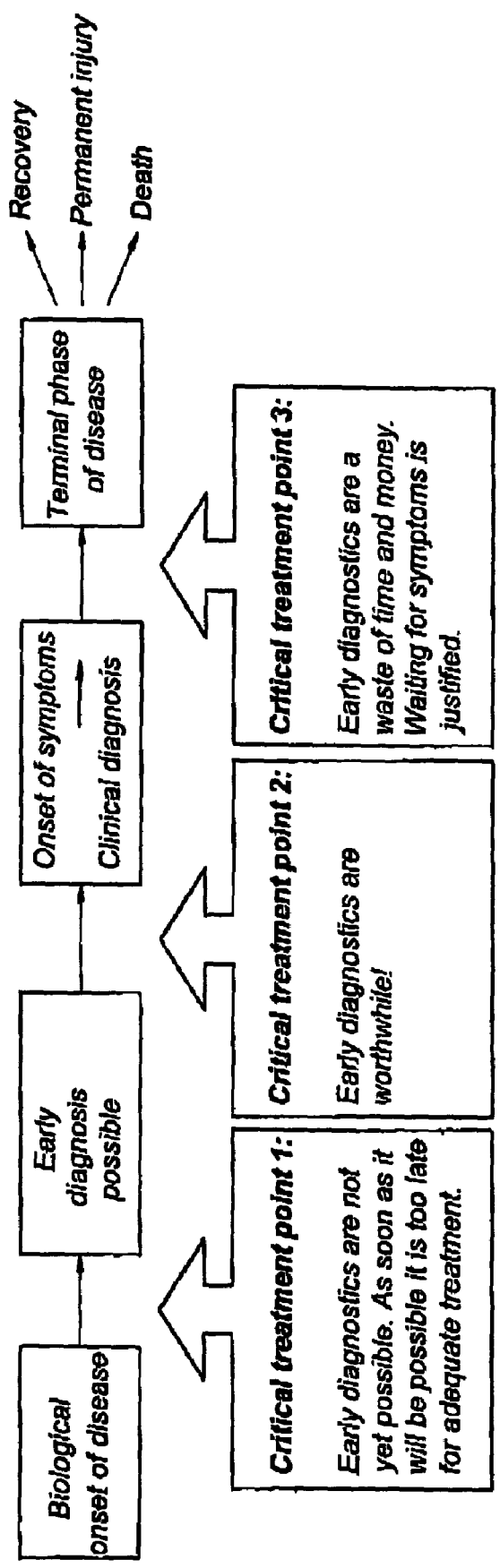
FIG. 8 shows critical points in the natural course of a disease.
Figure 9:
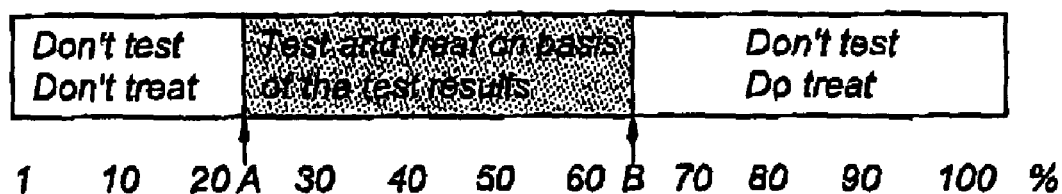
FIG. 9 shows how a test threshold and a treatment threshold can be defined.

In order to determine whether early diagnostics is worthwhile, it is then crucial to determine the critical treatment point(s) in the natural course of the disease; see FIG. 7. There is a transition point after which treatment is no longer effective, as is illustrated in more detail in FIG. 2. FIG. 2 shows a few critical points. These are:

Critical Point 1: Between the Biological Onset and the Time at Which Early Diagnostics are Possible The point at which effective treatment is (still) possible has already been passed before early diagnostics are possible. In this case early diagnostics will thus be possible too late to still be of help.

Critical Point 3: Between the Onset of Symptoms and the Final Stage of the Disease In this case it is equally as effective (and the patient feels ill for a shorter time) to wait for the onset of symptoms and until the patient seeks clinical help. Early diagnostics will only be waste of time and money.

Critical Point 2: Between the Time at Which Early Diagnostics are Possible and the Onset of Symptoms Only when the critical point of the disease is here is there a possibility of a beneficial influence on the end stage of the disease with the aid of early diagnostics.

Step 3: The Benefit of Early Diagnostics for the Individual Patient

The purpose of step 3 is, given the disease that was the subject of the early diagnostic evaluation, to be able to determine per patient whether early diagnostics will be worthwhile.

For this purpose the PreventionCompass 70 has been introduced here. In this the "threshold approach" of Stephan Pauker and Jerome Kassirer* [Pauker S. G. and Kassirer J. P. The threshold approach to clinical decision making. N. Engl. J. Med. 302: 1109, 1980] is linked to the validated risk algorithm as implemented in the PreventionCompass 70, so that an individual "cut off" for supplementary investigation can be determined in a reliable and statistically justified manner. Using this method it is possible, on the basis of the individual "pre-test likelihood" of disease, resulting from the personal risk profile, to calculate threshold values between which early diagnostics will be worthwhile for each person individually. This is further explained with reference to FIG. 3.

If the "pre-test likelihood" of disease is estimated to be below the "cut off" A (the "test threshold") it is so improbable that the person has the disease that neither supplementary diagnostics nor treatment will be beneficial. If, on the other hand, the "pre-test likelihood" of disease is estimated to be above the "cut off" B (the "treatment threshold") it is so probable that the person has the disease that treatment can be started immediately and therefore supplementary diagnostics are also not worthwhile. Only if the magnitude of the "pre-test likelihood" is estimated to be between "cut offs" A and B will supplementary diagnostics be valuable and treatment will ideally take place depending on the test result.

"The Threshold Approach":

In order to determine the two "cut off" values A and B, Pauker and Kassirer formulated a statistical formula based on a] the reliability of the diagnostic test, b] the safety of the diagnostic test, c] the effect of the treatment and d] the risk of treatment. In this formula account is taken of the fact that, depending on the reliability of the diagnostic tests, there is a risk of a false positive test result, as a result of which the patient will be unjustifiably treated and only the risk of damage from the diagnostics and/or treatment remains without any benefit.

The following definitions apply for this:

"adequate" treatment advantage: average benefit of the treatment (=treatment effect minus risks of the treatment) for patients with the disease, who are thus justifiably treated.

"inadequate" treatment risk: average risk of damage by serious complications of the treatment (risks of treatment) for patients without the disease who are thus unjustifiably treated.

diagnostic test risk: average risk of damage by serious complications of the diagnostic procedure.

likelihood of TP result: likelihood of true positive test result (sensitivity)

likelihood of FN result: likelihood of false negative test result (1-sensitivity)

likelihood of TN result: likelihood of true negative test result (specificity)

likelihood of FP result: likelihood of false positive rest result (1-specificity)

The "test threshold" (cut off A) is calculated via the following formula:

Test threshold =

$$\frac{(\text{likelihood of } FP \text{ result})(\text{"inadequate" treatment risk}) + (\text{diagnostic test risk})}{(\text{likelihood of } FP \text{ result})(\text{"inadequate" treatment risk}) + (\text{likelihood of } TP \text{ result})(\text{"adequate" treatment advantage})}$$

And the "treatment threshold" is calculated via the following formula:

$$\text{Test threshold} = \frac{(0.05) \times (0.02) + (0.001)}{(0.05) \times (0.02) + (0.9) \times (0.5)} = \frac{0.002}{0.46}$$

$$= 0.4\% \text{ ("pre-test likelihood" of disease)}$$

$$\text{Treatment threshold} = \frac{(0.95) \times (0.02) + (0.001)}{(0.95) \times (0.02) + (0.1) \times (0.5)} = \frac{0.02}{0.069}$$

$$= 29\% \text{ ("pre-test likelihood" of disease)}$$

Example: CT scan as early diagnostic aid for colon carcinoma for selection of patients who will benefit from an operation that is curative by design.

On the basis of the literature it can be stated that:
the advantage of early operation=50%
risk of complications from operation=2%
risk of complications from diagnostic test=0.1%
likelihood of TP result: 90%
likelihood of FN result: 10%
likelihood of TN result: 95%
likelihood of FP result: 5%

Treatment threshold =

$$\frac{(\text{likelihood of } TN \text{ result})(\text{"inadequate" treatment risk}) - (\text{diagnostic test risk})}{(\text{likelihood of } TN \text{ result})(\text{"inadequate" treatment risk}) + (\text{likelihood of } FN \text{ result})(\text{"adequate" treatment advantage})}$$

Figure 10:
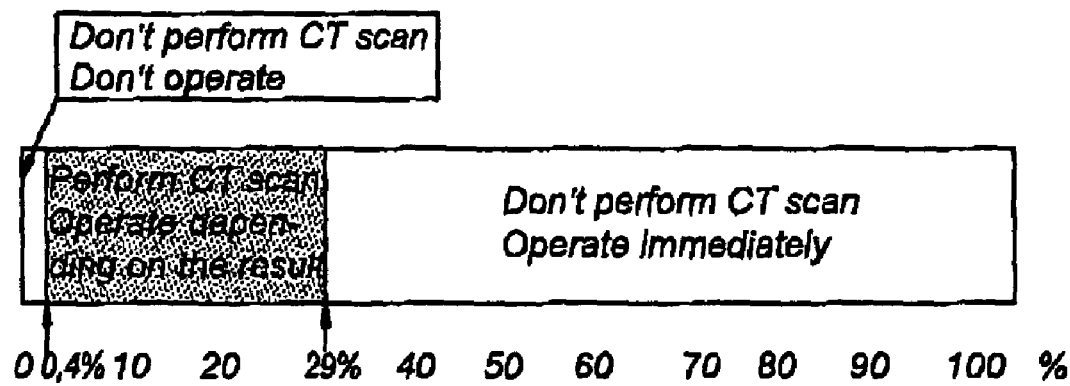
FIG. 10 gives a practical example of FIG. 9.

On the basis of these calculations "the decision diagram" is as shown in FIG. 10:

Step 4: Quality Control by Continuous Evaluation

Step 4 serves as quality control on the early diagnostic policy implemented. This is effected by continuous evaluation to answer the following questions:

A. Does early diagnosis actually lead to improved clinical outcomes (in terms of survival, functioning and quality of life)?

B. After there good facilities in the present care system for people who test positive?

C. Do persons who test positive follow the treatment and prevention advice?

D. Are the cost effectiveness and the number of false positive and/or negative results socially acceptable?

The 4-Step Plan in Practice: CT Scan as an Example of an Early Diagnostic Test

With the aid of Steps 1 and 2 (see above) it becomes clear that (according to current insights) early diagnostics using a CT scan could be beneficial in the oncological field for evaluation of the following presymptomatic malignant processes:

Colon carcinoma
Lung carcinoma
Cervical carcinoma
Mammary carcinoma

In the field of heart and vascular diseases the (multislice) CT scan could be beneficial for "fine-tuning" a likelihood of a future atherosclerotic complication determined by the Personal Risk Profile, such as:

Coronary heart diseases (including heart failure)
Ischaemic cerebral diseases (stroke)
Abdominal and thoracic aneurisms
Metabolic syndrome (determination of the intra-abdominal fat level)
(Peripheral vascular complaints)

It is still too early to be able to determine the benefit of the CT scan as an early diagnostic test for other complaints or it is clear that this test is of no value in this area. Therefore, when evaluating the CT images obtained only the abovementioned complaints will be looked for and potential other complaints will be blanked out by means of a sophisticated "screen".

With the aid of the PreventionCompass mentioned in Step 3 the test threshold and treatment threshold for the CT scan as an early diagnostic test are calculated in the server 55 for the abovementioned complaints and linked to the personal risk algorithm by means of which the individual "pre-test likelihood" of disease is determined. If the PreventionCompass indicates that the "pre-test likelihood" of disease exceeds the test threshold for one or more of the abovementioned complaints, a CT scan will be recommended via the PreventionPassport 72.

The results of such a CT scan are then sent to the server 55 as "laboratory test data" 64 and the PreventionPassport 72 is adjusted on the basis of these. On the basis of the contents thereof, a physician can act as he/she thinks fit in respect of this (these) complaint(s), i.e. refer (to 2nd line healthcare) for treatment in the case of a positive test result and not refer (except for possible preventive measures) in the case of a negative test result.

With the aid of the results 64 of the CT scan the server 55 is now also able to evaluate whether there are indications for the presence or absence of the other abovementioned complaints (which thus did not reach the test threshold in the first instance). It should be clear that the reliability of a positive scan result for these complaints is lower (because of the lower "pre-test likelihood") than for the complaint(s) which did reach the test threshold. The risk of a false positive test result for these complaints is accordingly so high that automatic treatment on the basis of this result will be associated with overtreatment and will be unjustified. However, because of the statistical relationship between the "pre-test likelihood" and the "post-test likelihood" (=positive predictive value) it is now possible, with the aid of the sensitivity and specificity of the CT scan (known from the literature) for the "detected" complaint, to calculate the actual likelihood of the presence of the disease more reliably. This can be illustrated easily on the basis of a "2 by 2 table".

For example:
Pre-test likelihood=1:1000 (=the "pre-test likelihood" resulting from the Personal Risk Profile)
Sensitivity=90%
Specificity=96%

| 2 by 2 table | | | |
|---|---|---|---|
| | Disease | | |
| Test result | Present | Absent | |
| Positive | 9 | 400 | 409 |
| Negative | 1 | 9,590 | 9,591 |
| | 10 | 9,990 | 10,000 |

→ post-test likelihood (positive predictive value) = 9:409 = 2.2%

The likelihood that the disease is actually present has now become 2.2%.

For the follow-up route the "pre-test likelihood" of this complaint is thus now 2.2% instead of 0.1%.

If the "pre-test likelihood" of disease has now become so high that the "treatment threshold" is exceeded, treatment can be started immediately. If this is not the case, supplementary testing will be indicated. The most appropriate supplementary diagnostic test for this specific individual can now be sought easily and reliably on the basis of the "new" pre-test likelihood. This is carried out by determining the "test thresholds" (with the aid of step 3) for the various potentially useful diagnostic test(s) and evaluating whether this threshold is exceeded by the "new" pre-test likelihood for this (these) test(s). If this is the case for several tests, the most ideal test can be chosen taking into account differences in patient friendliness and cost effectiveness.

Fictional Practical Example 55 year old male smoker with a positive family anamnesis for lung cancer, a blood pressure of 120/80 mmHg and a cholesterol plasma level of 6 mmol/l.

On the basis of the Personal Risk Profile, based on the algorithms for cancer and atherosclerosis, the "pre-test likelihood" of the abovementioned complaints for this man is as follows (in the following calculations the figures are as yet fictitious and intended solely for illustration):

In respect of oncological complaints:

---
colon carcinoma: 1:200 = 0.2%
lung carcinoma: 1.5:100 = 1.5%
etc.

---

In respect of atherosclerosis and the associated risk of complications:
likelihood of coronary infarction within the next 10 years: 15%
likelihood of CVA [CVA=cerebrovascular accident] within the next 10 years: 6%
AAA/ATA [AAA/ATA=aneurism of abdominal aorta/aneurism of thoracic aorta]: 0.15%

The "test threshold" for a CT scan for the various complaints is:
For oncological complaints:
colon carcinoma: 0.4%
lung carcinoma: 1.3%
etc.

In respect of atherosclerosis and the associated risk of complications:
likelihood of coronary infarction within the next 10 years: 9%
likelihood of CVA within the next 10 years: 7.5%
AAA/ATA: 0.6%

N.B.: Here the following are chosen as outcome criterion for a positive CT scan result:
in respect of colon carcinoma: tumour>0.5 cm
in respect of lung carcinoma: tumour>0.5 cm
in respect of likelihood of coronary infarction: coronary stenosis>70%
in respect of CVA: previous cerebral infarctions can be demonstrated
in respect of AAA/ATA: aorta diameter 5 and 6 cm, respectively.

It follows from the above that for lung carcinoma the "test threshold" for carrying out a CT scan has been reached and the "treatment threshold" is not exceeded. It is thus worthwhile in the case of this patient to carry out an early diagnostic examination with the aid of a CT scan to evaluate the "target complaint" lung carcinoma. On the basis of the test and treatment thresholds, CT scanning will be worthwhile in the case of this patient for evaluation of the degree of atherosclerosis and the associated likelihood of future atherosclerotic complications as well.

Assume that the result of the CT scan in respect of the abovementioned complaints is as follows:
no indications of a lung carcinoma
suspicion of colon carcinoma
left coronary artery>70% stenosis
no previous cerebral infarctions
no AAA/ATA This result means that a lung carcinoma is as good as excluded and no further diagnostic tests and/or treatment is indicated. An aneurism is also excluded.

The fact that there are indications for a colon carcinoma does not mean that this actually also exists. Because the "pre-test likelihood" of this complaint was low (below the "test threshold"), the risk of a false positive result is relatively high. Immediate treatment (for example by means of keyhole surgery and optional operative resection) would be associated with an unnecessary risk of complications at the individual level and unnecessarily high costs at population level.

However, the "post-test likelihood" can be calculated using the previously determined "pre-test likelihood" and the sensitivity and the specificity of the CT scan for an asymptomatic colon carcinoma. By this means it is then possible to determine whether a stressful treatment will nevertheless be permissible or whether initially further supplementary diagnostics are indicated and, if so, with which diagnostic test this should ideally be carried out.

Colon Carcinoma:

"pre-test likelihood" = 2:1000 (0.2%)
sensitivity = 90%
specificity = 95%

2 by 2 table

| Test result | Disease Present | Disease Absent | |
|---|---|---|---|
| Positive | 18 | 499 | 517 |
| Negative | 2 | 9,481 | 9,483 |
| | 20 | 9,980 | 10,000 |

→ post-test likelihood (positive predictive value) = 18:517 = 3.5%

The treatment threshold is thus not reached and it is thus sensible to perform supplementary tests in order actually to demonstrate any tumour. The most ideal test in the sense of reliability, patient friendliness and cost effectiveness can then be chosen on the basis of the test and treatment criteria for the other available diagnostic tests for colon carcinoma, such as faeces occult blood testing (FOBT), barium meal colon inflow image and coloscopy. In practice such a patient will be referred to the 2nd line care specialist on the basis of this test result, where he/she will most probably be given a diagnostic coloscopy.

With regard to atherosclerosis, the previously determined "pre-test likelihood" of a future coronary infarction was: 5% in 10 years. The post-test likelihood of a future infarction on the basis of the CT result is therefore calculated as follows:

Atherosclerosis:

"pre-test likelihood" = 15:100 (15%)
sensitivity = 85%
specificity = 85%

2 by 2 table

| Test result | Disease Present | Disease Absent | |
|---|---|---|---|
| Positive | 128 | 127 | 255 |
| Negative | 22 | 723 | 745 |
| | 150 | 850 | 1,000 |

→ post-test likelihood (positive predictive value) = 128:255 = 50%

According to the international prevention consensus the treatment threshold for medicaments is: 20% in 10 years.

Therefore, preventive treatment will be indicated.

Scope of Disease Profiles for the First Stage

The strategy outlined above has been used for the identification of complaints and associated screening techniques for the first stage. It has been found from this listing and evaluation that early diagnostics for diseases is a highly active area of technological development and applied medical research.

The application of the 'morbidity and mortality criterion' (Step 1, criterion A) has resulted in the following provisional list of complaints:

Oncological diseases:
Colon carcinoma
Lung carcinoma
Mammary carcinoma
Prostate carcinoma
Skin cancer
Cervical carcinoma
(various intra-abdominal types of cancer; cancer of the head/neck region)
Atherosclerotic heart and vascular diseases:
Coronary heart diseases (including heart failure)
Ischaemic cerebral diseases (stroke)
Abdominal aneurism
(peripheral vascular complaints)
Oncological Complaints The proposition developed here is based on the vision that in the case of cancer there is a 'window of opportunity' for cure in the period between the onset of malignancy and the stage in which the disease has metastasised and usually can no longer be cured. Detection of the tumour within this 'window', followed by adequate medical treatment can be expected to lead to a more advantageous outcome than waiting until the tumour manifests itself clinically.

As described above, it is proposed to follow a two-step approach that first of all involves the determination of a personal risk profile on the basis of:

Age (the most important risk factor for cancer)
Sex (for sex-related tumours)
Hereditary (family) aspects
Specific risk factors for specific types of cancer On the basis of this personal risk profile it is established (as described above in Step 3) whether someone has such an increased risk that exposure to a potentially harmful imaging technique and to the possible harmful (side) effect of the treatment in the case of a positive test is justified.

The imaging techniques that can be considered for each disease can differ. There are various instrumental techniques (for example CT, MRI, X-ray) and new laboratory tests (genomics, proteomics) that in principle are able to detect early tumours. As yet spiral CT appears to be a highly promising technique for the early detection of lung tumours, colon tumours (virtual colonoscopy) and other intra-thoracic or intra-abdominal malignancies. MRI appears to be highly promising for the early detection of breast cancer and for virtual colonoscopy.

Heart and Vascular Diseases

The abovementioned specific heart and vascular diseases are essentially different forms of expression (complications) of one common pathophysiological entity called atherosclerosis, the 'common denominator'. Atherosclerosis is a process that progresses slowly and initially proceeds asymptomatically. It is usually only after a long time that symptoms (for example angina pectoris, claudication) arise or there is an abrupt complication in the form of a coronary infarction, a stroke, a TIA or rupture of an aneurysm. Sometimes such a complication is fatal, but to an increasing extent patients are surviving such an 'event' (as a result of continuous improvement in acute treatment). However, patients who survive a first 'event' often have serious limitations or loss of function (think of stroke) and have an appreciably higher likelihood of being affected by an 'event' again, developing heart failure and/or dying prematurely.

Epidemiological research, such as the known American Framingham study and the recently completed European PROCAM and SCORE studies, have shown that atherosclerosis and the adverse consequences thereof are promoted by the presence of specific risk factors. Screening for a number of these universally accepted risk factors can be carried out using simple techniques, such as:

Anamnesis (age, sex, overweight, smoking, family burden, exercise)

Physical diagnostic test (high blood pressure)

Simple (finger prick) blood tests (high cholesterol, diabetes)

On the basis of the results of the abovementioned studies various risk algorithms have been formulated by means of which the (absolute) risk of a future serious atherosclerotic complication can be determined. In the course of time these risk algorithms have evolved from simple algorithms with relatively few parameters to more complex methods in which more risk factors are taken into account.

In view of the virtually non-stressful nature of the diagnostic methods required for such cardiovascular risk profiling (anamnesis, blood pressure measurement, blood tests) and the high "negative predictive value", known algorithms of this type are sent to the server 55 as diagnostic methods 65 and stored in the database 71 in the server. The server 55 uses these risk algorithms to determine the Personal Risk Profile of a client. In addition, the server 55 uses these risk algorithms to estimate the pre-test likelihood of disease that is incorporated in the PreventionPassport, so that it is then possible to determine, with the aid of the method described in Step 3 (see above), whether supplementary early diagnostic tests would be beneficial.

As shown in FIG. 11, histological changes (for example hypertrophy of the left ventricle, calcification of the coronary arteries, thickening of the intima media and the carotid artery) can already be determined using special techniques some considerable time before atherosclerosis becomes clinically manifest. The degree of atherosclerosis can be quantified with the aid of these early diagnostic techniques (with a broad spread in reliability).

These methods can be subdivided into:

Imaging Techniques

Electron beam CT (calcification score for the coronary vessels)

Multislice CT angiography (stenosis of the coronaries of more than 50%)

Intima media thickness (IMT) determination on the carotid artery (atherosclerotic burden)

Echography of the heart (hypertrophy of the left ventricle, wall movement malfunctions)

CT angiography of the thoracic and abdominal aorta (evaluation of aneurisms).

Functional Techniques

Endothelial function evaluating techniques (FMD)

Ergometric tests (walking test and exercise stress electrocardiography).

To an increasing extent there are indications from studies that a number of these techniques have a predictive value for the likelihood of a serious cardiovascular event. Current opinion, therefore, is also that a number of these methods can be offered as a supplement to persons at high risk as a supplement to simple risk profiling to establish whether atherosclerosis has already progressed to such an extent that treatment is indicated. Data of this type can be stored in the database 71 and taken into account in the calculations performed by server 55.

The coronary calcification score, with the aid of electron beam CT, would, for example, have additional value in the case of patients at medium high risk on the basis of the Framingham risk assessment [P. Greenland, et al. *JAMA*, 2004; 209: 210-215]. Further "fine tuning" of the actual risk of a future cardiovascular event is extremely welcome in this group of patients in particular in order to be able to make a correct choice between starting or not starting preventive (platelet-inhibiting) treatment with medicaments.

In the case of persons with a relevant isolated risk factor (for example hypertension) it would also be possible to establish in secondary screening whether there are already signs of terminal organ damage, such as:

Hypertrophy of left ventricle (ECG)

Microalbuminuria (urine determination)

Retinopathy (findoscopy)

The addition of these diagnostic techniques as a supplementary second step to the "simple" risk profiling as is used to date in the medical field for symptom-free persons brings the future closer by means of a contribution to the design and/or performance of research in this context.

The invention claimed is:

1. A telecommunication system to compose a personal report comprising a central computer installation with a knowledge system and a plurality of other computer installations, the plurality of other computer installations comprising at least a first computer installation arranged to receive healthcare related data from an individual, at least a second computer installation arranged to receive physical, diagnostic and laboratory test data from the individual, and a third computer installation arranged to receive healthcare related scientific data, the central computer installation comprising an input/output unit for communicating with the plurality of other computer installations, a processor, and memory with data and instructions stored therein so that the processor can execute a predetermined program, wherein the predetermined program is arranged to enable the processor:

to receive at least anamnesis data for the individual from the first computer installation;

to receive physical, diagnostic and laboratory test data for the individual from the second computer installation;

to receive healthcare related scientific data comprising data on diagnostics methods and data on use of medication or treatment methods with regard to predetermined diseases from the third computer installation;

to calculate an integrated and personal risk profile of the individual's likelihood of a disease, based on the at least anamnesis data received from the first computer, the physical, diagnostic examination and laboratory test data for the individual from the second computer installation, and the healthcare related scientific data from the third computer installation;

to calculate a test threshold and a treatment threshold which are both based on the at least anamnesis data received from the first computer; the physical, diagnostic and laboratory test data for the individual from the second computer installation, and the healthcare related scientific data from the third computer installation;

to calculate whether a risk of the individual acquiring the diseases in the future is below the test threshold, between the test threshold and the treatment threshold or above the treatment threshold and if the risk of the individual acquiring the disease is below the test threshold, to include in a personal report that a further test is not needed and medical treatment is not necessary;

the risk of the individual acquiring the disease is between the test threshold and the treatment threshold, to include in the personal report that a further test relating to the disease is needed and medical treatment is dependent on the further test; or said risk of the individual acquiring the disease is above the treatment threshold, to include in the personal report that further medical intervention is necessary.

2. The telecommunication system according to claim 1, wherein the predetermined program is further arranged to enable the processor to receive characterological characteristics of the individual, and based on the characterological characteristics of the individual to incorporate the characterological characteristics and determine the motivation and persistence regarding advice on a healthy lifestyle in the personal report.

3. The telecommunication system according to claim 1, wherein the predetermined program is further arranged to enable the processor to receive financial/economic data from the third computer installation, wherein the financial/economic data is accounted for in a calculation during the composition of the personal report.

4. The telecommunication system according to claim 1, wherein the predetermined diseases comprise oncological diseases, atherosclerotic heart and vascular diseases, and degenerative diseases.

5. The telecommunication system according to claim 1, wherein the risk of the individual acquiring the disease in the future is calculated before the onset of symptoms.

6. The telecommunication system according to claim 1, wherein the predetermined program is further arranged to enable the processor to store the personal report in a database in the memory of the central computer installation.

7. The telecommunication system according to claim 1, wherein the predetermined program is further arranged to enable the processor to establish a research report comprising medicine based evidence data, and to send the research report comprising medicine based evidence data back to the third computer installation to allow for updating the healthcare related scientific data.

8. The telecommunication system according to claim 7, wherein the program is further arranged to enable the processor to store the research report comprising medicine based evidence data in a database in the memory of the central computer installation.

9. The telecommunication network according to claim 7, wherein the risk of the individual acquiring the predetermined disease in the future, harbouring the disease or having the disease is calculated before an onset of symptoms.

10. The telecommunication system according to claim 1, wherein the personal report further comprises at least one risk factors relating to one of the predetermined disease; advice on lifestyle or medicine; or data on the disease.

11. The telecommunication system according to claim 1, wherein the test threshold and the treatment threshold depend at least on reliability of the further test, safety of the further test, effect of the medical treatment, risk of the medical treatment, and preference data of the individual.

12. The telecommunication system according to claim 1, wherein A) the test threshold is defined as:

$$\frac{(\text{likelihood of FP result})(\text{``inadequate'' treatment risk} + \text{Prx}) + (\text{diagnostic test risk})}{(\text{likelihood of FP result})(\text{``inadequate'' treatment risk} + \text{Prx}) + (\text{likelihood of TP result})(\text{``adequate'' treatment advantage} + \text{Pnrx})}$$

B) the treatment threshold is defined as:

$$\frac{(\text{likelihood of TN result})(\text{``inadequate'' treatment risk} + \text{Prx}) - (\text{diagnostic test risk})}{(\text{likelihood of TN result})(\text{``inadequate'' treatment risk} + \text{Prx}) + (\text{likelihood of FN result})(\text{``adequate'' treatment advantage} + \text{Pnrx})}$$

wherein:
"adequate" treatment advantage is defined as average benefit of the medical treatment for the individuals with the disease, who are thus justifiably treated;
"inadequate" treatment risk is defined as average risk of damage by serious complications of the medical treatment for the individuals without the disease who are thus unjustifiably treated;
diagnostic test risk is defined as average risk of damage by serious complications of the further test;
likelihood of TP result is defined as likelihood of true positive test result;
likelihood of EN result is defined as likelihood of false negative test result;
likelihood of TN result is defined as likelihood of true negative test result;
likelihood of FP result is defined as likelihood of false positive rest result;
Prx is defined as individuals degree of concern about unnecessary measures in case that the disease is absent; and
Pnrx is defined as individuals degree of concern about withholding measures in case that the disease is present; and
C) the medical treatment data relates to a supplementary diagnostic to arrive at a definitive diagnosis, an alternative diagnostic technique with comparable results, or a treatment method.

13. The telecommunication system according to claim 1, wherein the processor is further arranged to receive updated data from the first computer installation and the second computer installation and update the personal report accordingly.

14. The telecommunication system according to claim 1, wherein the processor is further arranged to receive data on a diagnostic method, use of medication or a treatment method corresponding to a predetermined disease from the third computer installation.

15. The telecommunication system according to claim 1, wherein the research report further comprises evidence based medicine data.

16. A central computer installation having a computer readable medium having stored thereon data and instructions which, when executed by a processor of the computer, causes the central computer installation to function as part of a telecommunication system to compose a personal report comprising a central computer installation with a knowledge system and a plurality of other computer installations, the plurality of other computer installations comprising at least a first computer installation arranged to receive healthcare related data from an individual, at least a second computer installation arranged to receive physical, diagnostic and laboratory test data from the individual, and a third computer installation arranged to receive healthcare related scientific data, the central computer installation comprising an input/output unit for communicating with the plurality of other computer installations, a processor, and memory with data and instructions stored therein so that the processor can execute a predetermined program, wherein the predetermined program is arranged to enable the processor:
- to receive at least anamnesis data for the individual from the first computer to receive physical, diagnostic and laboratory test data for the individual from the second computer installation;
- to receive healthcare related scientific data comprising data on diagnostics methods and data on use of medication or treatment methods with regard to predetermined diseases from the third computer installation;
- to calculate an integrated and personal risk profile of the individual's likelihood of a disease, based on the at least anamnesis data received from the first computer, the physical, diagnostic examination and laboratory test data for the individual from the second computer installation, and the healthcare related scientific data from the third computer installation;
- to calculate a test threshold and a treatment threshold which are both based on the at least anamnesis data received from the first computer: the physical, diagnostic and laboratory test data for the individual from the second computer installation, and the healthcare related scientific data from the third computer installation;
- to calculate whether a risk of the individual acquiring the diseases in the future is below the test threshold, between the test threshold and the treatment threshold or above the treatment threshold and if
  - the risk of the individual acquiring the disease is below the test threshold, to include in a personal report that a further test is not needed and medical treatment is not necessary;
  - the risk of the individual acquiring the disease is between the test threshold and the treatment threshold, to include in the personal report that a further test relating to the disease is needed and medical treatment is dependent on the further test; or
- said risk of the individual acquiring the disease is above the treatment threshold, to include in the personal report that further medical intervention is necessary.

17. A method of composing a personal report by utilizing a telecommunication system to compose a personal report comprising a central computer installation with a knowledge system and a plurality of other computer installations, the plurality of other computer installations comprising at least a first computer installation arranged to receive healthcare related data from an individual, at least a second computer installation arranged to receive physical, diagnostic and laboratory test data from the individual, and a third computer installation arranged to receive healthcare related scientific data, the central computer installation comprising an input/output unit for communicating with the plurality of other computer installations, a processor, and memory with data and instructions stored therein so that the processor can execute a predetermined program, wherein the predetermined program is arranged to enable the processor:
- to receive at least anamnesis data for the individual from the first computer installation;
- to receive physical, diagnostic and laboratory test data for the individual from the second computer installation;
- to receive healthcare related scientific data comprising data on diagnostics methods and data on use of medication or treatment methods with regard to predetermined diseases from the third computer installation;
- to calculate an integrated and personal risk profile of the individual's likelihood of a disease, based on the at least anamnesis data received from the first computer, the physical, diagnostic examination and laboratory test data for the individual from the second computer installation, and the healthcare related scientific data from the third computer installation;
- to calculate a test threshold and a treatment threshold which are both based on the at least anamnesis data received from the first computer; the physical, diagnostic and laboratory test data for the individual from the second computer installation, and the healthcare related scientific data from the third computer installation;
- to calculate whether a risk of the individual acquiring the diseases in the future is below the test threshold, between the test threshold and the treatment threshold or above the treatment threshold and if
  - the risk of the individual acquiring the disease is below the test threshold, to include in a personal report that a further test is not needed and medical treatment is not necessary;
  - the risk of the individual acquiring the disease is between the test threshold and the treatment threshold, to include in the personal report that a further test relating to the disease is needed and medical treatment is dependent on the further test; or
- said risk of the individual acquiring the disease is above the treatment threshold, to include in the personal report that further medical intervention is necessary, the method comprising:
- receiving at least anamnesis data for an individual from the first computer installation;
- receiving physical and diagnostic data and data from laboratory investigation for the individual from the second computer installation;
- receiving healthcare related scientific data comprising data on diagnostic methods and data on use of medication and treatment methods with regard to predetermined diseases from the third computer installation;
- calculating an integrated and personal risk profile of the individual's likelihood of disease, including the risk of the individual acquiring one of the predetermined diseases in the future, based on at least anamnesis data received from the first computer, the physical and diagnostic examination and data from laboratory investigation for the individual from the second computer installation, and the healthcare related scientific data from the third computer installation;
- calculating a test threshold and a treatment threshold which are both based on at least anamnesis data received from the first computer, the physical and diagnostic examination and data from laboratory investigation for the individual from the second computer installation, and the healthcare related scientific data from the third computer installation, calculating whether the risk of the individual acquiring the predetermined diseases in the future is below the test threshold, between the test threshold and the treatment threshold or above the treatment threshold and if the risk of the individual acquiring the disease in the future is below the test threshold, including in a personal report that a further test is not needed and medical treatment is not necessary;

the risk of the individual acquiring the disease in the future is between the test threshold and the treatment threshold, including in the personal report that a further test relating to the disease is needed and medical treatment is dependent on the further test;

the risk of the individual acquiring the disease in the future is above the treatment threshold, including in the personal report that further medical intervention is necessary.

18. The method according to claim 17, wherein the risk of the individual acquiring the predetermined disease is calculated before an onset of symptoms.

19. The method according to claim 17, further comprising establishing a research report comprising medicine based evidence data; and sending the research report back to the third computer installation to update the healthcare related scientific data.

20. The method according to claim 17, further comprising receiving characterological characteristics of the client and incorporating characterological characteristics and determining motivation and persistence regarding advice on a healthy lifestyle based on the characterological characteristics of the individual in the personal report.

21. The method according to claim 17, further comprising receiving financial/economic data from the third computer installation and utilizing the financial/economic data in composing the personal report.

22. A data carrier provided with a computer program product having stored thereon data and instructions that can be loaded in the memory by a computer installation having a processor and a memory, which when executed by a processor of the computer, causes the processor to perform a method of composing a personal report by utilizing a telecommunication system to compose a personal report comprising a central computer installation with a knowledge system and a plurality of other computer installations, the plurality of other computer installations comprising at least a first computer installation arranged to receive healthcare related data from an individual, at least a second computer installation arranged to receive physical, diagnostic and laboratory test data from the individual, and a third computer installation arranged to receive healthcare related scientific data, the central computer installation comprising an input/output unit for communicating with the plurality of other computer installations, a processor, and memory with data and instructions stored therein so that the processor can execute a predetermined program, wherein the predetermined program is arranged to enable the processor:

to receive at least anamnesis data for the individual from the first computer installation;

to receive physical, diagnostic and laboratory test data for the individual from the second computer installation;

to receive healthcare related scientific data comprising data on diagnostics methods and data on use of medication or treatment methods with regard to predetermined diseases from the third computer installation;

to calculate an integrated and personal risk profile of the individual's likelihood of a disease, based on the at least anamnesis data received from the first computer, the physical, diagnostic examination and laboratory test data for the individual from the second computer installation, and the healthcare related scientific data from the third computer installation;

to calculate a test threshold and a treatment threshold which are both based on the at least anamnesis data received from the first computer: the physical, diagnostic and laboratory test data for the individual from the second computer installation, and the healthcare related scientific data from the third computer installation;

to calculate whether a risk of the individual acquiring the diseases in the future is below the test threshold, between the test threshold and the treatment threshold or above the treatment threshold and if the risk of the individual acquiring the disease is below the test threshold, to include in a personal report that a further test is not needed and medical treatment is not necessary;

the risk of the individual acquiring the disease is between the test threshold and the treatment threshold, to include in the personal report that a further test relating to the disease is needed and medical treatment is dependent on the further test; or said risk of the individual acquiring the disease is above the treatment threshold, to include in the personal report that further medical intervention is, the method comprising:

receiving at least anamnesis data for an individual from the first computer installation;

receiving physical and diagnostic data and data from laboratory investigation for the individual from the second computer installation;

receiving healthcare related scientific data comprising data on diagnostic methods and data on use of medication and treatment methods with regard to predetermined diseases from the third computer installation;

calculating an integrated and personal risk profile of the individual's likelihood of disease, including the risk of the individual acquiring one of the predetermined diseases in the future, based on at least anamnesis data received from the first computer, the physical and diagnostic examination and data from laboratory investigation for the individual from the second computer installation, and the healthcare related scientific data from the third computer installation;

calculating a test threshold and a treatment threshold which are both based on at least anamnesis data received from the first computer, the physical and diagnostic examination and data from laboratory investigation for the individual from the second computer installation, and the healthcare related scientific data from the third computer installation, calculating whether the risk of the individual acquiring the predetermined diseases in the future is below the test threshold, between the test threshold and the treatment threshold or above the treatment threshold and if the risk of the individual acquiring the disease in the future is below the test threshold, including in a personal report that a further test is not needed and medical treatment is not necessary;

the risk of the individual acquiring the disease in the future is between the test threshold and the treatment threshold, including in the personal report that a further test relating to the disease is needed and medical treatment is dependent on the further test;

the risk of the individual acquiring the disease in the future is above the treatment threshold, including in the personal report that further medical intervention is necessary.

23. A telecommunication system to compose a personal report comprising a central computer installation with a knowledge system and a plurality of other computer installations the plurality of other computer installations comprising at least a first computer installation arranged to receive healthcare related data from an individual, at least a second computer installation arranged to receive physical, diagnostic and laboratory test data from the individual, and a third computer installation arranged to receive healthcare related scientific data, the central computer installation comprising an input/output unit for communicating with the plurality of other computer installations, a processor, and memory with data and instructions stored therein so that the processor can execute a predetermined program, wherein the predetermined program is arranged to enable the processor to receive at least anamnesis data for the individual from the first computer installation, to receive physical, diagnostic and laboratory test data investigation for the individual from the second computer installation, to receive healthcare related scientific data comprising data on a diagnostic method and data on use of medication or treatment method with regard to a predetermined disease from the third computer installation, to calculate an integrated and personal risk profile of the individual's likelihood of disease, including a risk of the individual acquiring the disease in the future, harbouring the disease or having the disease, based on at least anamnesis data received from the first computer, the physical, diagnostic and laboratory test data from laboratory investigation for the individual from the second computer installation, and the healthcare related scientific data from the third computer installation to calculate a test threshold and a treatment threshold which are both based on at least anamnesis data received from the first computer, the physical, diagnostic and laboratory test data for the individual from the second computer installation, and the healthcare related scientific data from the third computer installation to calculate whether the risk of the individual acquiring the diseases, harbouring the disease or having the disease is below the test threshold, between the test threshold and the treatment threshold or above the treatment threshold and if the risk of the individual acquiring the predetermined diseases in the future, harbouring the disease or having the disease is below the test threshold, to include in the personal report that a further test is not needed and medical treatment is not necessary;

the risk of the individual acquiring the disease, harbouring the disease or having the disease is between the test threshold and the treatment threshold, to include in the personal report that a further test relating to the disease is needed and medical treatment is dependent on the further test;

the risk of the individual acquiring the diseases, harbouring the disease or having the disease is above the treatment threshold, to include in the personal report that further medical intervention is necessary to calculate data with regard to a possible prevention program for the individual to prevent the predetermined disease and include the prevention program data in the personal report;

to calculate data with regard to a medication to combat the disease that may be harboured or existing and include the medication data in the personal report; and to produce the personal report as output.

24. A method of composing a personal report by utilizing a telecommunication network, the telecommunication network comprising a central computer installation with a knowledge system and a plurality of other computer installations, the plurality of other computer installations comprising at least a first computer installation arranged to receive healthcare related data from an individual, at least a second computer installation arranged to receive physical, diagnostic and laboratory test data the individual, and a third computer installation arranged to receive healthcare related scientific data, the method comprising:

receiving at least anamnesis data for the individual from the first computer installation, receiving physical, diagnostic, and laboratory test data for the individual from the second computer installation, receiving healthcare related scientific data comprising data on diagnostics methods and data on use of a medication or a treatment method with regard to the disease from the third computer installation, calculating an integrated and personal risk profile of the individual's likelihood of disease, including the risk of the individual acquiring the disease in the future, harbouring the disease or having the disease, based on at least anamnesis data received from the first computer, the physical, diagnostic, and laboratory test data for the individual from the second computer installation, and the healthcare related scientific data from the third computer installation calculating a test threshold and a treatment threshold that are both based on at least anamnesis data received from the first computer, the physical, diagnostic, and laboratory test data for the individual from the second computer installation, and the healthcare related scientific data from the third computer installation calculating whether the risk of the individual the disease, harbouring the disease or having the disease is below the test threshold, between the test threshold and the treatment threshold or above the treatment threshold and if the risk of the individual acquiring the disease, harbouring the disease or having the disease is below the test threshold, including in a personal report that a further test is not needed and medical treatment is not necessary;

the risk of the individual acquiring the disease, harbouring the disease or having the disease is between the test and treatment threshold, including in the personal report that the further test relating to the disease is needed and the medical treatment is dependent on the further test;

the risk of the individual acquiring the diseases, harbouring the disease or having the disease is above the treatment threshold, including in the personal report that further medical intervention is necessary;

calculating data with regard to a possible prevention program for the individual to prevent the disease and including the prevention program data in the personal report;

calculating data with regard to a medication to combat the disease that may be harboured or existing and including the medication data in the personal report; and producing the personal report as output.

25. The method according to claim 24, wherein the risk of the individual acquiring the disease, harbouring the disease or having the disease is calculated before an onset of symptoms.

* * * * *

UNITED STATES PATENT AND TRADEMARK OFFICE
CERTIFICATE OF CORRECTION

PATENT NO. : 7,650,290 B2
APPLICATION NO. : 11/080339
DATED : January 19, 2010
INVENTOR(S) : Van Kalken et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1178 days.

Signed and Sealed this

Twenty-third Day of November, 2010

David J. Kappos
*Director of the United States Patent and Trademark Office*